(12) United States Patent
Burgmeier

(10) Patent No.: US 6,200,290 B1
(45) Date of Patent: Mar. 13, 2001

(54) DILATATION BALLOONS CONTAINING POLYESTERETHERAMIDE COPOLYMER

(75) Inventor: Robert E. Burgmeier, Plymouth, MN (US)

(73) Assignee: Schneider (USA) Inc., Plymouth, MN (US)

(*) Notice: Subject to any disclaimer, the term of this patent is extended or adjusted under 35 U.S.C. 154(b) by 0 days.

(21) Appl. No.: 09/041,176

(22) Filed: Mar. 12, 1998

Related U.S. Application Data

(62) Division of application No. 08/931,256, filed on Sep. 16, 1997, now abandoned, which is a division of application No. 08/906,126, filed on Aug. 5, 1997, now abandoned, and a continuation of application No. 08/449,048, filed on May 24, 1995, now abandoned.

(51) Int. Cl.$^7$ .................................................. A61M 29/00
(52) U.S. Cl. ...................... 604/96.01; 604/104; 428/37.5
(58) Field of Search ...................... 604/96–104; 606/192, 606/194; 428/37.5; 600/470

(56) References Cited

U.S. PATENT DOCUMENTS

| | | |
|---|---|---|
| 4,154,244 | 5/1979 | Becker et al. . |
| 4,254,774 | 3/1981 | Boretos . |
| 4,331,786 | 5/1982 | Foy et al. . |
| 4,332,920 | 6/1982 | Foy et al. . |
| 4,385,635 | 5/1983 | Ruiz . |
| 4,413,989 | 11/1983 | Schejeldahl et al. . |
| 4,490,421 | 12/1984 | Levy . |
| 4,563,181 | 1/1986 | Wijayarathna et al. . |
| 4,675,361 | 6/1987 | Ward, Jr. . |
| 4,786,556 | 11/1988 | Hu et al. . |
| 4,820,270 | 4/1989 | Hardcastle et al. . |
| 4,886,506 | 12/1989 | Lovegren . |
| 4,898,591 | 2/1990 | Jang et al. . |
| 4,906,244 | 3/1990 | Pinchuk et al. . |

(List continued on next page.)

FOREIGN PATENT DOCUMENTS

| | | |
|---|---|---|
| 697219 A2 | 2/1983 | (EP) . |
| 117093 A3 | 8/1984 | (EP) . |
| 274411 A2 | 7/1988 | (EP) . |
| 513459 A1 | 11/1992 | (EP) . |
| 537069 A1 | 4/1993 | (EP) . |
| 540858 A1 | 5/1993 | (EP) . |

(List continued on next page.)

OTHER PUBLICATIONS

Atochem, "PEBAX Polyether Block Amide" (Dec. 1987), pp. 1–22.
Huls America Inc. "Engineering Thermoplastics" (Oct. 1988), pp. 1–88.
Flesher, "Polyether block amide, high–performance TPE," Modern Plastics, Sep. 1987, pp. 100,105,106 and 110.
Dupont, "Hytrel®" 11p. product brochure dated 10/91.
Koch, "Pebax (Polyether Block Amide)", Advances in Polymer Technology, vol. 2 No. 3, 1982 pp. 160–162.
De, et al, eds. Thermoplastic Elastomer from Rubber–Plastic Blends, Chaptyer 1, Ellis Horwoal, New York pp. 13–27.
Gorski, "The Nomenclature of Thermoplastic Elastomers," Kunststoffe German Plastics, 83 (1993) No. 3, pp. 29–30.
Hofmann, "Thermoplastic Elastomers," Kunstsoffe German Plastics, 80 (1990) No. 10, pp. 88–90.
Atochem, "Pebax® Resins 33 Series Property Comparison" undated, (1 p. manufacturers technical information sheet received Sep. 29, 1994).
Atochem, undated and untitled brochure for Pebax® resins, pp. 2–5.

Primary Examiner—Sharon Kennedy
Assistant Examiner—Michael M Thompson
(74) Attorney, Agent, or Firm—Vidas, Arrett & Steinkraus

(57) ABSTRACT

Disclosed is a dilatation balloon having a single layer containing polyesteretheramide copolymer. The dilatation balloon may also contain polyamide and/or additional polymers, and may contain substantially no polyetheramide having substantially no ester linkages.

11 Claims, 8 Drawing Sheets

U.S. PATENT DOCUMENTS

| | | |
|---|---|---|
| 4,917,667 | 4/1990 | Jackson . |
| 4,938,676 | 7/1990 | Jackowski et al. . |
| 4,950,239 | 8/1990 | Gahara et al. . |
| 4,950,257 | 8/1990 | Hibbs et al. . |
| 4,952,357 | 8/1990 | Euteneuer . |
| 4,964,853 | 10/1990 | Sugiyama et al. . |
| 4,994,032 | 2/1991 | Sugiyama et al. . |
| 5,108,415 | 4/1992 | Pinchuk et al. . |
| 5,156,612 | 10/1992 | Pinchuk et al. . |
| 5,226,880 | 7/1993 | Martin . |
| 5,236,659 | 8/1993 | Pinchuk et al. . |
| 5,246,420 | 9/1993 | Kraus et al. . |
| 5,250,069 | 10/1993 | Nobuyoshi et al. . |
| 5,264,260 | 11/1993 | Saab . |
| 5,281,677 | 1/1994 | Onwunaka et al. . |
| 5,290,306 | 3/1994 | Trotta et al. . |
| 5,295,978 | 3/1994 | Fan et al. . |
| 5,300,048 | 4/1994 | Drewes, Jr. et al. . |
| 5,304,134 | 4/1994 | Kraus et al. . |
| 5,304,135 | 4/1994 | Shonk . |
| 5,304,197 | 4/1994 | Pinchuk et al. . |
| 5,304,340 | 4/1994 | Downey . |
| 5,328,468 | 7/1994 | Kaneko et al. . |
| 5,334,148 | 8/1994 | Martin . |
| 5,335,675 | 8/1994 | Wheeler, deceased et al. . |
| 5,342,386 | 8/1994 | Trotta . |
| 5,344,400 | 9/1994 | Kaneko et al. . |
| 5,348,538 | 9/1994 | Wang et al. . |
| 5,358,486 | 10/1994 | Saab . |
| 5,397,306 | 3/1995 | Nobuyoshi et al. . |
| 5,433,713 | 7/1995 | Trotta . |
| 5,500,180 | 3/1996 | Anderson et al. . |
| 5,545,133 * | 8/1996 | Burns et al. ............................ 604/96 |
| 5,554,120 * | 9/1996 | Chen et al. ............................. 604/96 |
| 5,556,383 * | 9/1996 | Wang et al. ............................ 604/96 |
| 5,565,523 | 10/1996 | Chen et al. . |
| 5,747,591 | 5/1998 | Chen et al. . |
| 5,830,182 | 11/1998 | Wang et al. . |
| 5,849,846 | 12/1998 | Chen et al. . |
| 5,879,369 * | 3/1999 | Ishida .................................... 604/96 |
| 5,921,957 * | 7/1999 | Killion et al. ......................... 604/96 |

FOREIGN PATENT DOCUMENTS

| | | |
|---|---|---|
| 420488 B1 | 7/1993 | (EP) . |
| 566755 A1 | 10/1993 | (EP) . |
| 592885 A2 | 4/1994 | (EP) . |
| 2651681 | 2/1983 | (FR) . |
| 58-188463 | 11/1983 | (JP) . |
| 8401513 | 4/1984 | (WO) . |
| 9001345 | 2/1990 | (WO) . |
| 9208512 | 5/1992 | (WO) . |
| 9219316 | 11/1992 | (WO) . |
| 9523619 | 9/1995 | (WO) . |

OTHER PUBLICATIONS

Bhowmick, et al, eds. Handbook of Thermoplastic Elastomers, Chapters 10 and 12, Marcel Dekker Inc., pp. 344–373 and 411–442.

Walker, et al, eds. Handbook of Thermoplastic Elastomers, Chapter 8, Van Nostrand Reinhold Co., NY pp. 258–281.

M. Xie, et al, "Etude Morphologique De Bloc–Copoly-(ether–Amide)s," Makromol. Chem 187 (1985 pp. 383–400.

H. Boubil, et al., "Morphology of Polyamide and Polyether Block Amide Blends," Polymer Engineering and Science, 29, pp. 679–684 (1989).

N. Alberola, et al, "Mechanical Relaxation Processes in Polyether Block Amide Copolymers (PEBA)," Makromol. Chem, Makromol, Symp. 23, pp. 219–224 (1989).

H. Faruque, et al, "Study of Multiple Relaxations in PEBAX, Polyether Block Amide (PA 12 2135 Block PTMG 2032), Copolymer Using the Thermally Stimulated Current Method," Polymer, 27, 527–531.

G. Gordon, "Glass Transition in Nylons," J. Polymer Sci.: Part A–2,9, pp. 1693–1702 (1971).

D.Prevorsek, et al, "Mechanical Relaxations in Polyamides," J. Polymer Sci.: Part A–2, 9, 867–886 (1971).

H. Faruque, et al, "A Thermally Stimulated Current Technique for Measuring the Molecular Parameters of PEBAX, A Polymer–Block Amide Copolymer," J. Mater. Sci. 22, pp. 675–678 (1987).

N. Alberola, "Micromechanical Properties of polyether Block Amide Copolymers," J. Applied Sci., 36, pp. 787–804 (1988).

J. Brandrup, et al, eds., Polymer Handbook, John Wiley & Sons (1989), PP VI/209, VI/243–VI/244.

Serach Report in corresponding PCT application PCT/IB96/00291, and one–page Annex.

* cited by examiner

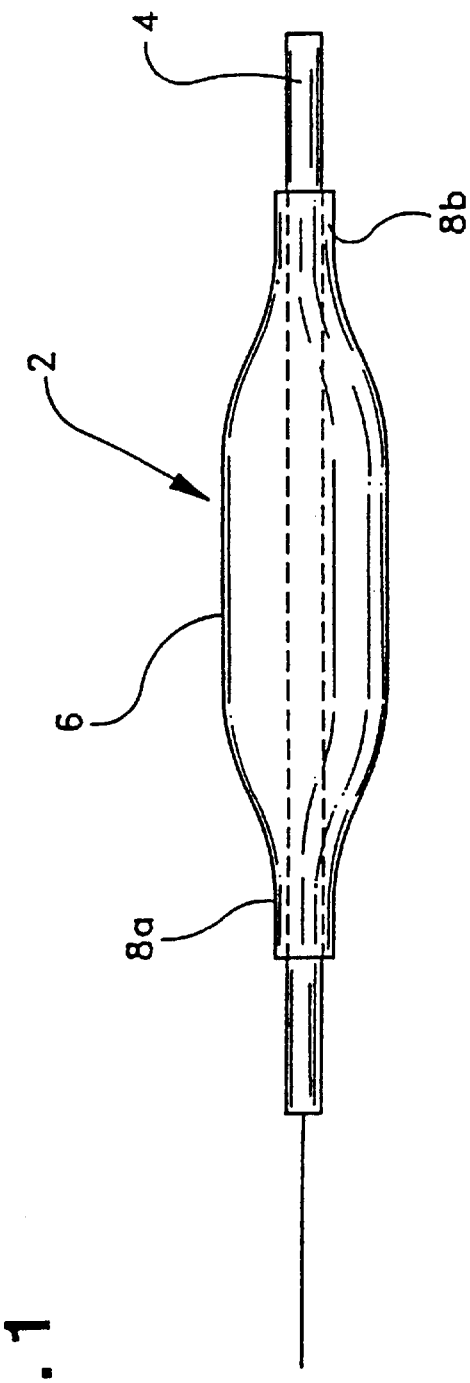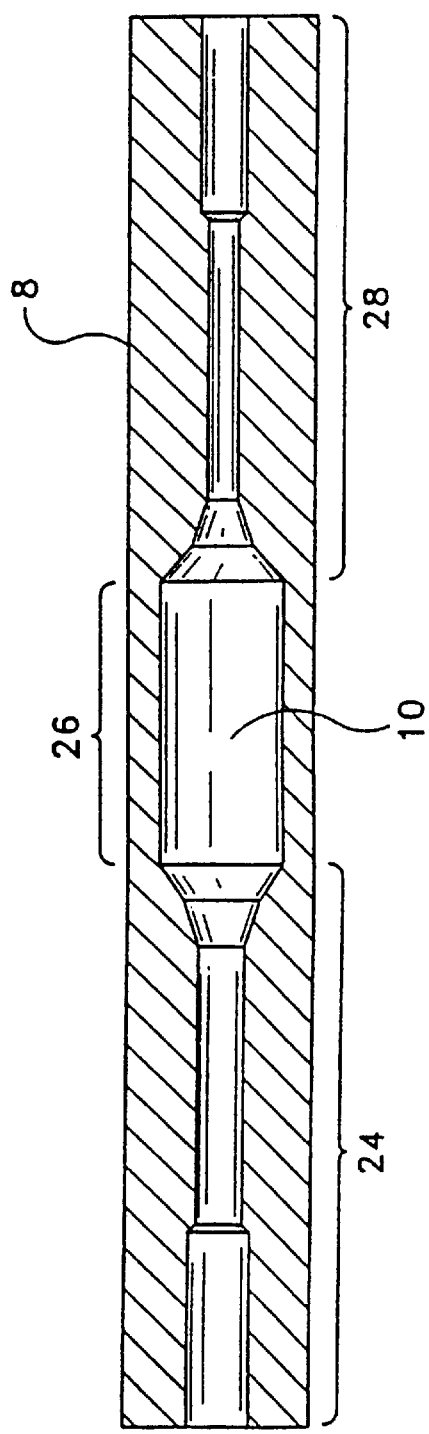
FIG. 1
FIG. 2

DILATATION BALLOONS CONTAINING POLYESTERETHERAMIDE COPOLYMER

This application is a divisional application of Ser. No. 08/931,256 filed Sep. 16, 1997, now abandoned, which is a divisional application of Ser. No. 08/906,126 filed Aug. 5, 1997 and is now abandoned, and is a continuation of Ser. No. 08/449,048 filed May 24, 1995 which is now abandoned.

BACKGROUND OF THE INVENTION

I. Field of the Invention

The present invention is generally directed to dilatation balloons containing polyesteretheramide copolymer.

II. Related Art

The use of balloon catheters for coronary angioplasty is known in the art. In an angioplasty procedure, a partially occluded blood vessel, i.e., one containing a stenosis, is treated by the use of an expanding balloon member which presses the stenosis back against the vessel wall. Typically, the expander member or balloon is carried on the distal end of a dilatation catheter which is routed through the vascular system to a location within, for example, a coronary artery containing a stenotic lesion. Following placement of the expander member across the lesion as desired, fluid is introduced into the proximal end of the catheter to inflate the expander member to a relatively high pressure, thereby restoring patency to the vessel. Coronary angioplasty procedures and angioplasty devices are described in detail in Vliestra et al., "Coronary Balloon Angioplasty," Blackwell Scientific Publications (1994).

Medical balloons that are known in the art are disclosed in the following documents: U.S. Pat. Nos. 4,964,853 and 4,994,032 to Sugiyama et al; U.S. Pat. Nos. 4,906,244, 5,108,415, 5,156,612, 5,236,659, and 5,304,197, to Pinchuk et al; U.S. Pat. Nos. 5,226,880 and 5,334,148 to Martin; U.S. Pat. No. 5,250,069 to Nobuyoshi et al; U.S. Pat. No. 5,328,468 to Kaneko et al.; European Patent Application No. 0 566 755; and Japanese laid-open patent application No. 58-188463. (All documents cited herein, including the foregoing, are incorporated herein in their entireties for all purposes.)

It is an object of the present invention to provide a balloon for an angioplasty device which is made, at least in part, of polyesteretheramide copolymer.

Other objects and advantages of the invention will become apparent to those skilled in the art through familiarization with the specification and claims herein.

SUMMARY OF THE INVENTION

In sum, the present invention relates to a balloon for an angioplasty device having a single polymeric layer. The layer may have from about 20 to about 100 weight percent polyesteretheramide copolymer and from about 0 to about 80 weight percent polyamide. The layer contains substantially no polyetheramide having substantially no ester linkages. The polyesteretheramide copolymer may be a block or random copolymer. The polyesteretheramide copolymer may have a hardness of from about 45 Shore D to about 78 Shore D, preferably from about 55 Shore D to about 75 Shore D, and more preferably from about 63 to about 72 Shore D. Even more preferably, the polyesteretheramide copolymer may have a hardness selected from about 63 Shore D, about 70 Shore D, and about 72 Shore D. The single polymeric layer may contain at least about 2 weight percent polyamide such as nylon 12, nylon 11, nylon 6, nylon 6/6, nylon 4/6, and combinations thereof. The single polymeric layer may further contain at least about 2 weight percent polymer such as polyester copolymer, polyurethane copolymer, polyethylene, and combinations thereof. The polymeric layer may have at least about 40 weight percent polyesteretheramide copolymer and more preferably at least about 80 weight percent polyesteretheramide copolymer. The balloon may have from about 20 to about 80 weight percent nylon 12 and about 20 to about 80 weight percent polyesteretheramide copolymer, preferably about 60 weight percent nylon 12 and about 40 weight percent polyesteretheramide copolymer. Alternatively, the balloon may have about 25 to about 80 weight percent nylon 4/6 and about 20 to about 75 weight percent polyesteretheramide copolymer, preferably about 65 weight percent nylon 4/6 and about 35 weight percent polyesteretheramide copolymer.

The present invention also relates to a balloon for an angioplasty device having a single polymeric layer consisting essentially of a polyesteretheramide copolymer. The polyesteretheramide copolymer may be a block or random copolymer. The polyesteretheramide copolymer may have a hardness of from about 45 Shore D to about 78 Shore D, preferably from about 55 Shore D to about 75 Shore D, and more preferably about 63 to about 72 Shore D. Even more preferably the polyesteretheramide copolymer may have a hardness selected from 63 Shore D, 70 Shore D, and 72 Shore D. The balloon may consist of polyesteretheramide.

The present invention also relates to a balloon for an angioplasty device having a single polymeric layer having (a) at least 91 weight percent polyesteretheramide copolymer, (b) from 0 to 9 weight percent polyamide, and (c) from 0 to 9 weight percent of a polymer other than polyesteretheramide and polyamide. The balloon may have at least about 95 weight percent polyesteretheramide copolymer.

DESCRIPTION OF THE DRAWINGS

FIG. 1 is a perspective view of an expander member of the present invention joined to the distal end of a catheter;

FIG. 2 is a cross-sectional view of a balloon form used to make expander members of the present invention;

DESCRIPTION OF THE PREFERRED EMBODIMENTS

Figure 3:
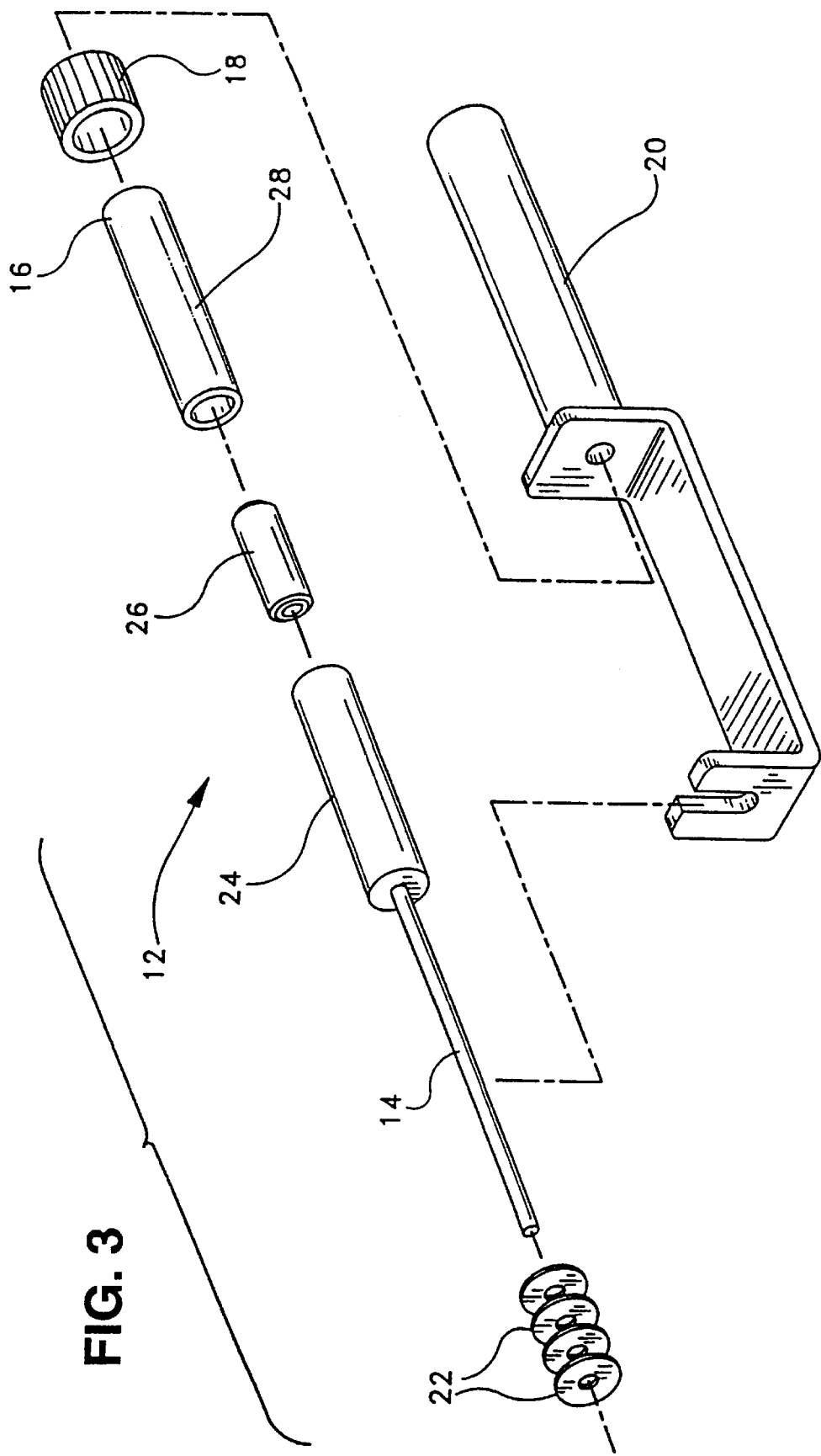
FIG. 3 is a schematic view of a mold apparatus used to make expander members of the present invention.
Figure 4:
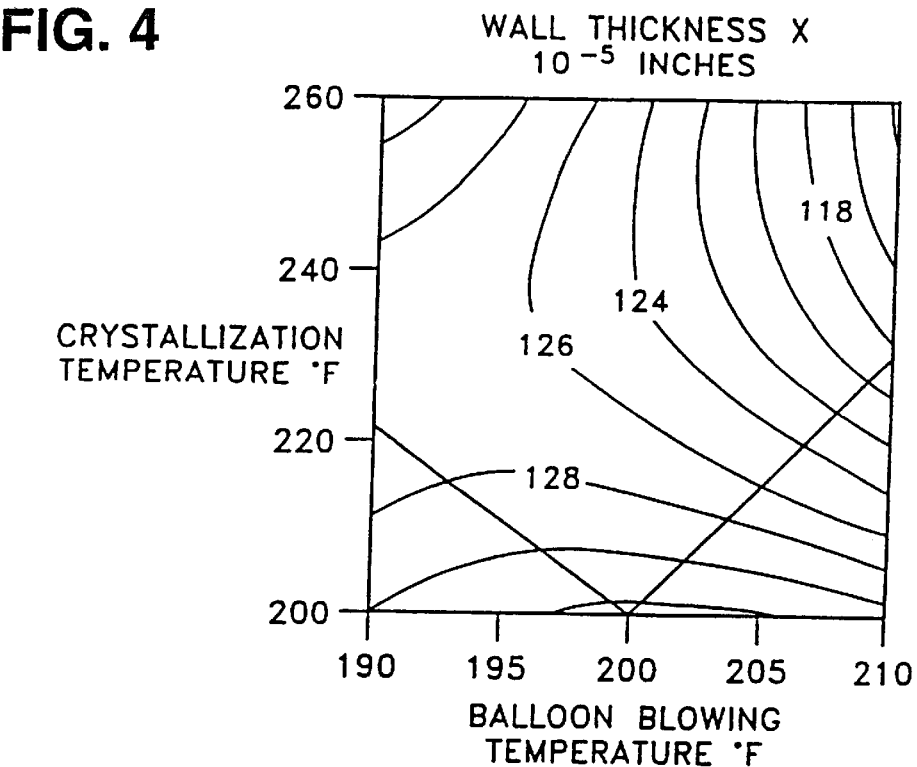
FIG. 4 shows a response surface that details the effects of processing variables and material selection on balloon wall thickness for PEBAX 6333 balloons.
Figure 5:
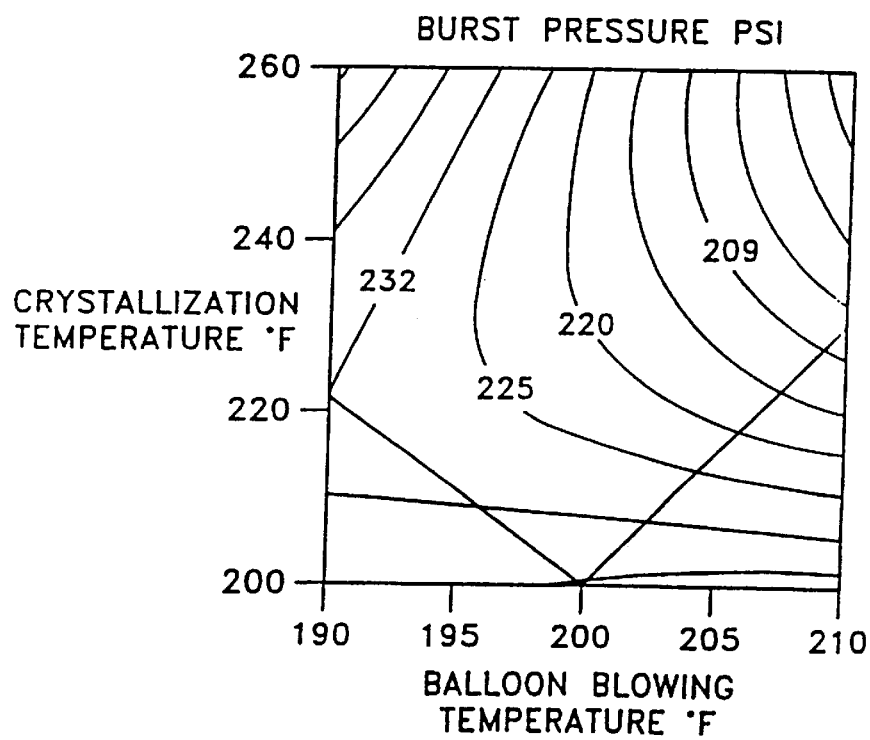
FIG. 5 shows a response surface that details the effects of processing variables and material selection on balloon burst pressure for PEBAX 6333 balloons.
Figure 6:
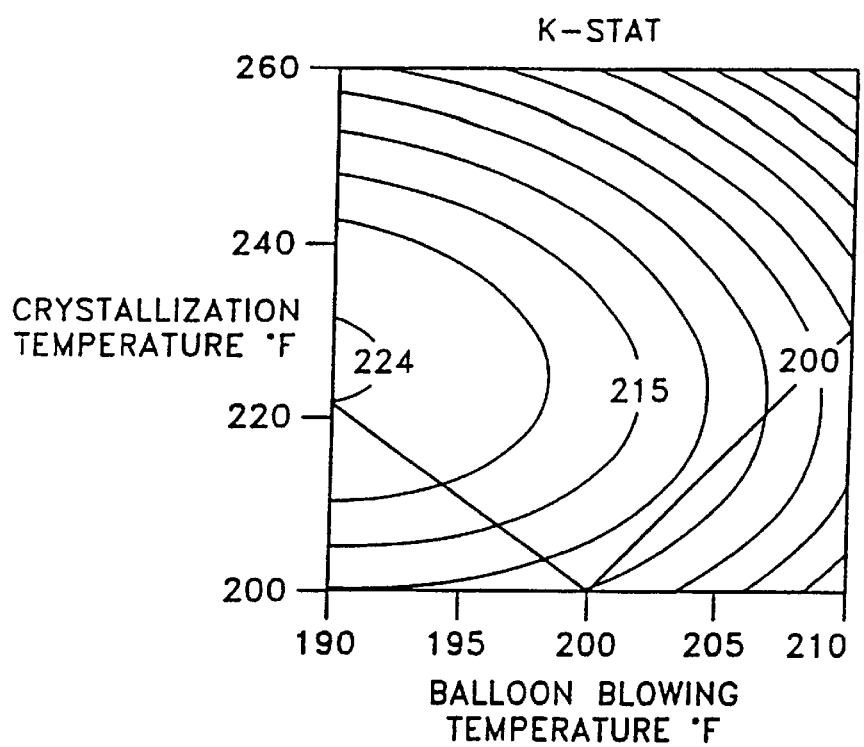
FIG. 6 shows a response surface that details the effects of processing variables and material selection on balloon K-stat for PEBAX 6333 balloons.
Figure 7:
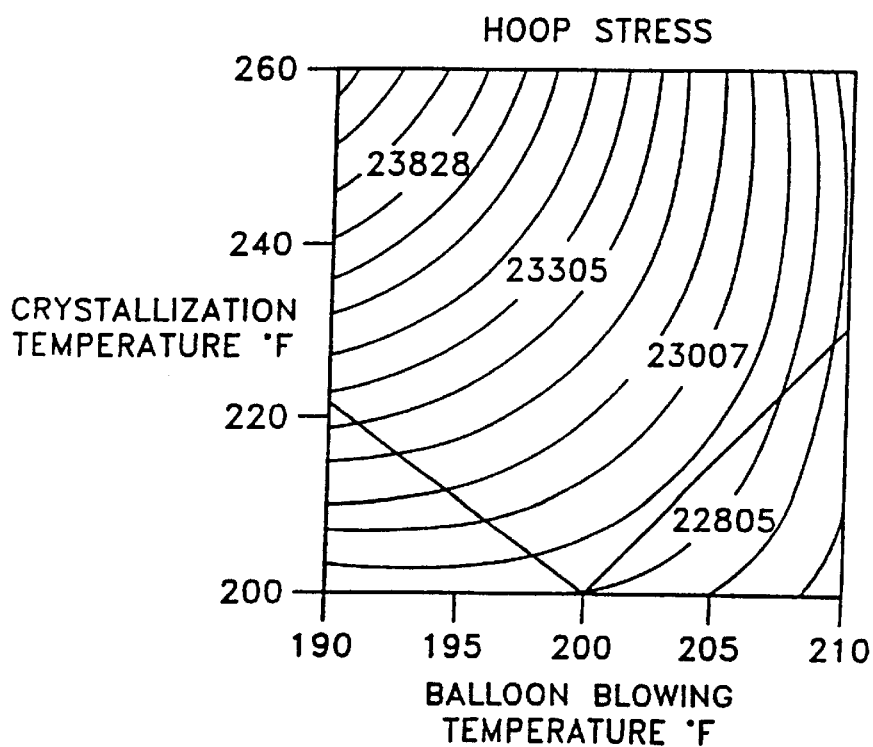
FIG. 7 shows a response surface that details the effects of processing variables and material selection on balloon hoop stress for PEBAX 6333 balloons.
Figure 8:
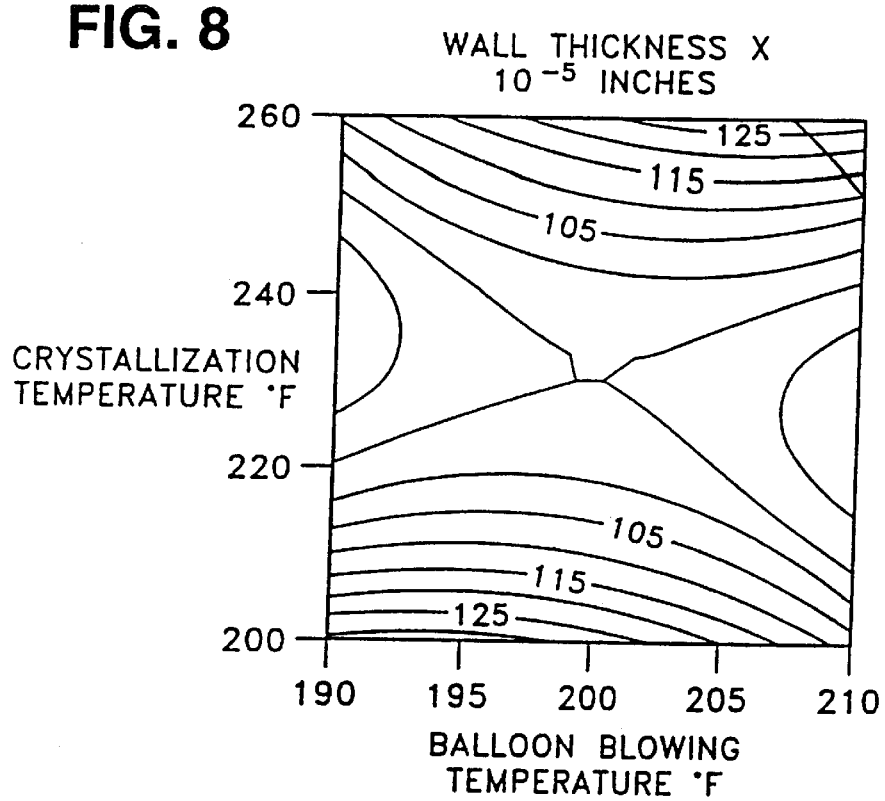
FIG. 8 shows a response surface that details the effects of processing variables and material selection on balloon wall thickness for PEBAX 7033 balloons.
Figure 9:
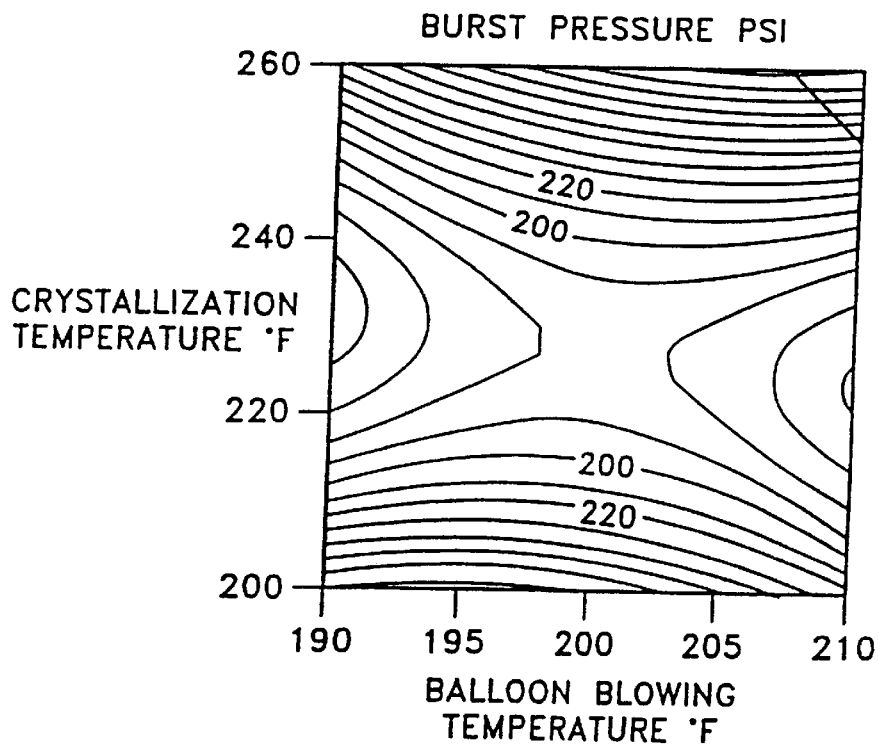
FIG. 9 shows a response surface that details the effects of processing variables and material selection on balloon burst pressure for PEBAX 7033 balloons.
Figure 10:
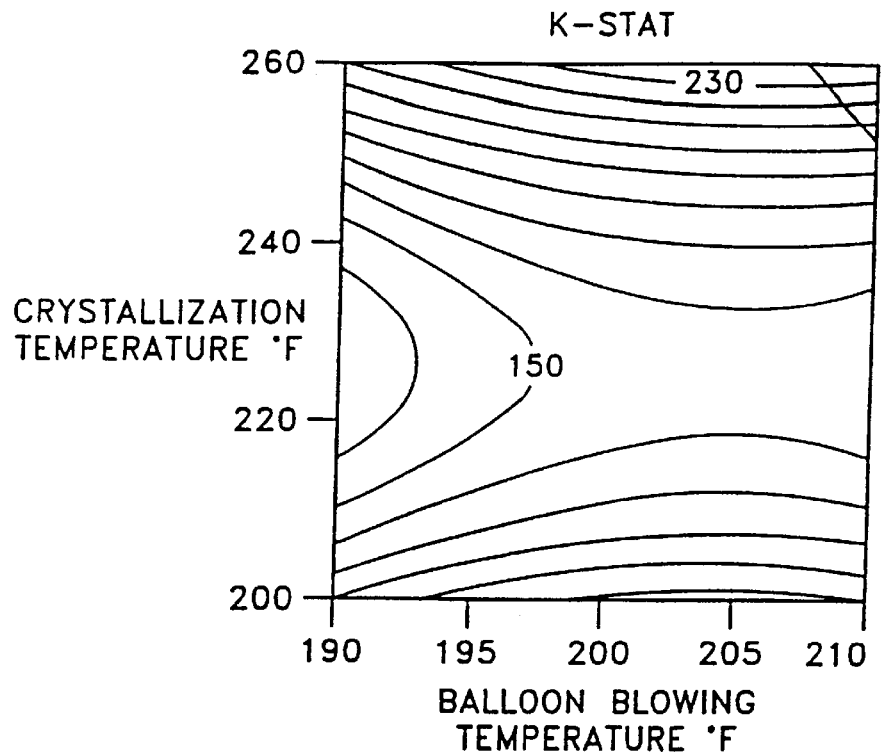
FIG. 10 shows a response surface that details the effects of processing variables and material selection on balloon K-stat 7033 for PEBAX 7033 balloons.
Figure 11:
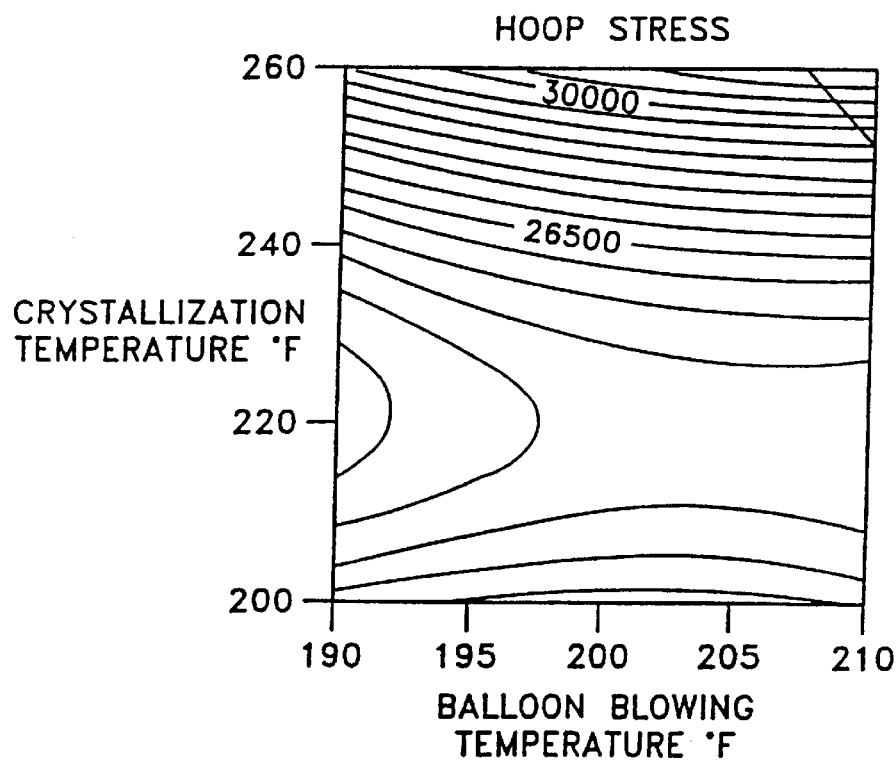
FIG. 11 shows a response surface that details the effects of processing variables and material selection on balloon hoop stress for PEBAX 7033 balloons.
Figure 12:
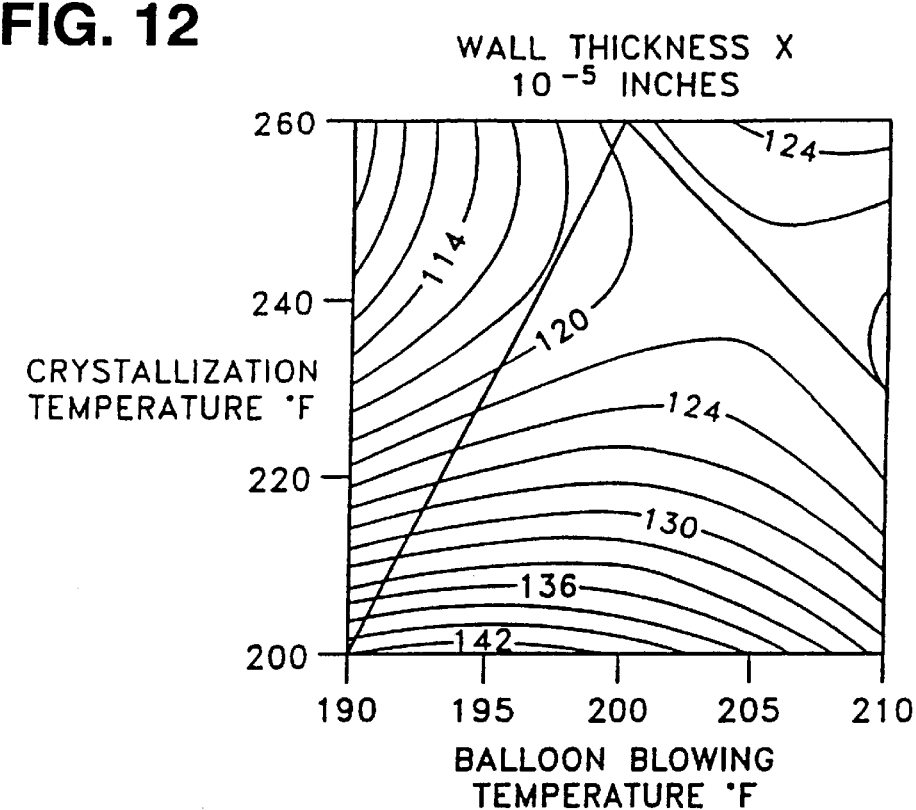
FIG. 12 shows a response surface that details the effects of processing variables and material selection on balloon wall thickness for PEBAX 7233 balloons.
Figure 13:
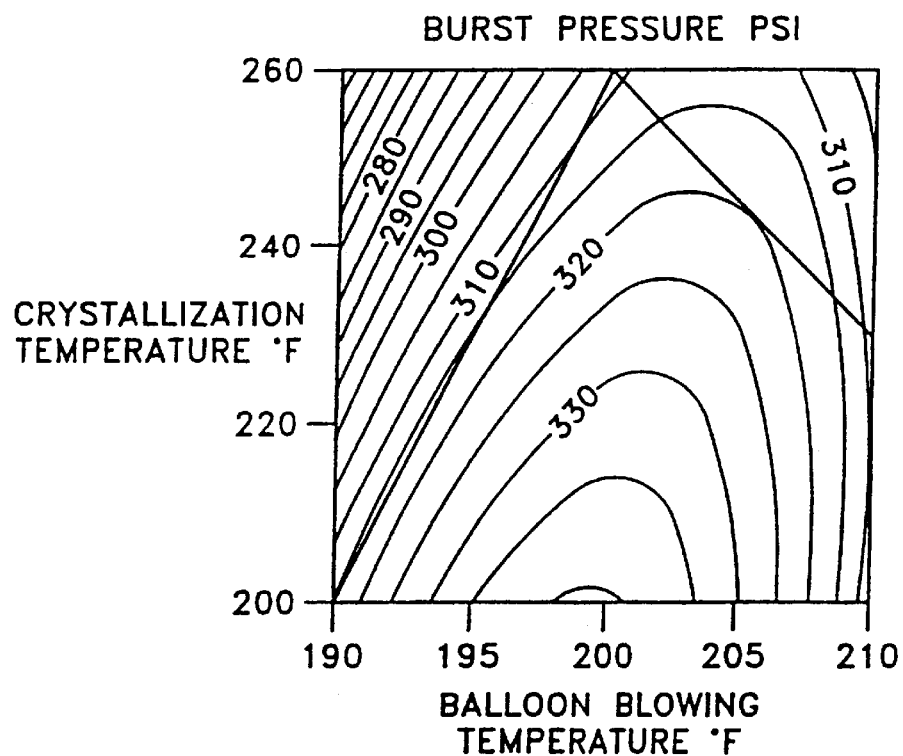
FIG. 13 shows a response surface that details the effects of processing variables and material selection on balloon burst pressure for PEBAX 7233 balloons.
Figure 14:
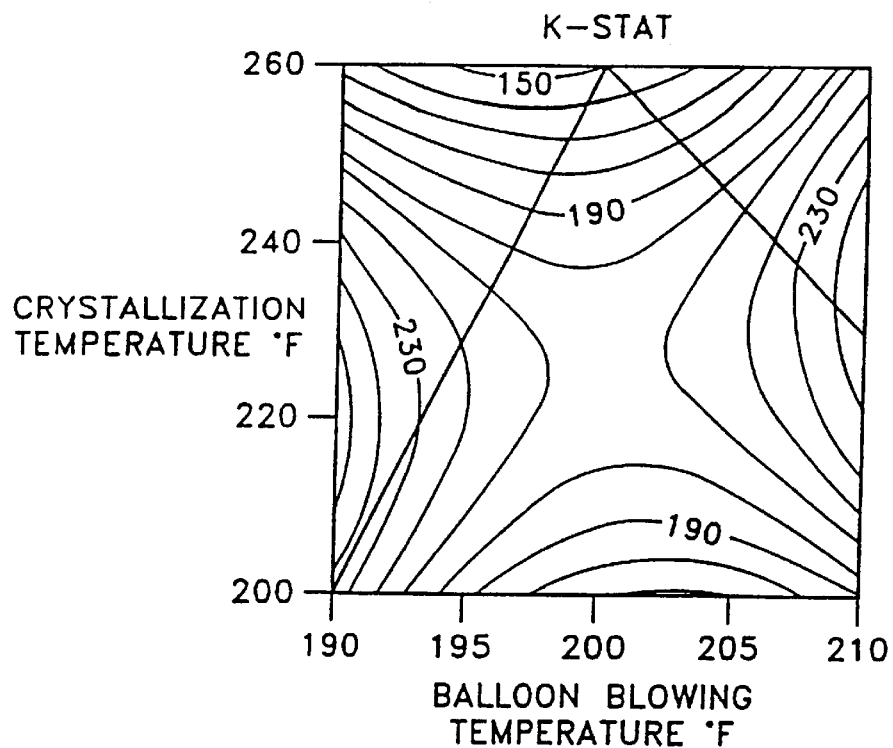
FIG. 14 shows a response surface that details the effects of processing variables and material selection on balloon K-stat for PEBAX 7233 balloons.
Figure 15:
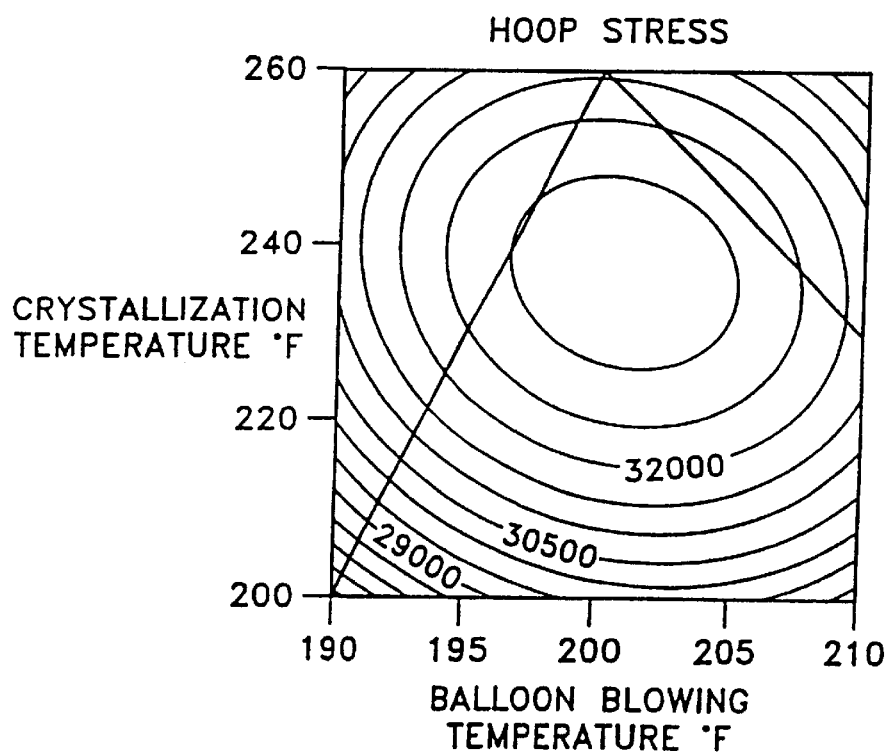
FIG. 15 shows a response surface that details the effects of processing variables and material selection on balloon hoop stress for PEBAX 7233 balloons.

With reference to FIG. 1, expander member 2 is attached to the distal end of a catheter shaft 4. The expander member 2, otherwise known as a balloon, has a single polymeric layer 6 which surrounds the catheter shaft 4. The expander member 2 shown is bonded at two bonding sites 8a,b by thermal bonding, by laser bonding, with adhesives, or by other methods known in the art.

The expander members of the present invention contain polyesteretheramide copolymer. The structure of these polymers consists of regular and linear chains of rigid polyamide blocks and flexible polyether blocks. Such copolymers may be described by the following formula:

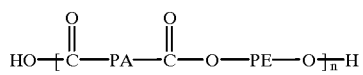

where PA is a polyamide block; and
where PE is a polyether block.

Polyesteretheramide copolymer materials are sold under the trademark PEBAX by Atochem Inc. of Glen Rock, N.J. Properties of several grades of PEBAX are disclosed in Atochem's brochure entitled "PEBAX Polyether Block Amide" (December 1987).

The expander member of the present invention may contain polyamide. Polyamide materials include nylon 12, nylon 11, nylon 6, nylon 6/6, and nylon 4/6. Such materials are sold under the trademark ZYTEL® by Dupont.

The expander member of the present invention may further contain a polymer other than polyesteretheramide copolymer or polyamide, such as polyester copolymer, polyurethane copolymer, polyethylene, and combinations thereof.

The single polymeric layer making up the expander member may be a blend of suitable materials. Such a blend may be created by mixing the desired resins and then extruding these resins to form a parison. The single layer can also be a graft copolymer. Such a graft copolymer can be formed, for example, by reacting polyamide (such as Nylon 12) with polyphenylether graft maleic anhydride (PPE-graft-MA). So called polymer alloys, and the like, are also included within the purview of this application.

The expander member of the present invention may be formed by first generating a parison in an extruder. The parison will typically have an inside diameter of from about 0.01 to 0.031 inches (0.025 to 0.079 cm), and a wall thickness of from about 0.0035 to 0.015 inches (0.0089 to 0.038 cm).

Hot water treated molding devices may then be utilized to blow mold the expander members of the present invention. Tubing of the desired material and having a required size and thickness is inserted into a balloon processing mold and heated to a temperature of from about 200–212° F. (93–100° C.). Weight may be added to the mold as desired. The tubing is subjected to longitudinal tension and high-pressure nitrogen 380–500 psi is introduced into the tubing in the mold. The mold remains in a hot water bath for a predetermined period of time of from about 10–45 seconds, preferably 25 seconds. The mold is then removed and placed in a cooling pot for a predetermined period of time of from about 20–40 seconds, preferably 30 seconds, after which the mold may be opened and the balloon removed.

In an alternative process, the balloons are formed in balloon blow molding machines. The tubing is inserted into the mold and the ends of the tubing secured into mold gaskets. The tubing is thereafter heated in the range of 190–220° F. (87–104° C.) for about 10 to 45 seconds, preferably 25–30 seconds, and the heated tubing is subjected to longitudinal tension and expanded 1–2 times its length in the axial direction. The stretched tubing is pressurized with nitrogen in the range of about 350–500 psi and heat treated in the mold for about 10–20 seconds at about 250–280° F. (121–138° C.), preferably about 260–270° F. (127–132° C.). The mold is then cooled to room temperature and allowed to set at room temperature in the mold under pressure for approximately 10 to 15 seconds. Thereafter, the system can be depressurized and the balloon removed from the mold.

EXAMPLES

Balloons were made of polyesteretheramide block copolymer and then tested to determine certain characteristics.

Examples 1–180

180 balloons were made according to the following process:

Parisons of 100 weight percent polyesteretheramide block copolymer were extruded. The parisons had inside diameters of about 0.015 inches to about 0.023 inches, wall thicknesses of about 0.006 inches to about 0.010 inches, and lengths of about 18 inches.

The parisons were placed in the mold apparatus illustrated in FIGS. 2 and 3. As shown in FIG. 2, the balloon form 8 had a void 10 corresponding to the final shape of the expander member. The void was made up by a proximal form 24, a body form 26, and a distal form 28. With reference to FIG. 3, the distal end of the parison was inserted into the proximal end 14 of the mold apparatus 12, and pushed through the proximal form 24, the body form 26, and the distal form 28 until it exited the distal end 16 of the mold section. Cap 18 was then placed over the distal end 16 of the apparatus 12 thereby clamping and sealing the distal end of the parison. The mold was then placed in a handle 20 such that the proximal end of the parison freely extended from the handle 20. Weights 22 were then placed over the proximal end of the parison and onto the mold.

The open proximal end of the parison was then connected to a pressurized nitrogen source by a Touhy Borst clamp. The nitrogen source was capable of achieving maximum pressures of 1,000 psi. The nitrogen source was then opened to varying degrees of between 350–500 psi and the mold was placed in a bath of hot water (212° F.).

The hot water bath warmed the parison. The freely extending proximal end of the parison was held by hand such that only about the distal form 28 was under water, until the mold dropped due to longitudinal stretching and the distal end of the parison expanded radially (about 15–30 seconds). Still holding the mold by hand, the mold continued to drop until it was entirely under water and the proximal end of the balloon expanded radially (about an additional 1–10 seconds).

The mold was then removed from the hot water bath and placed in a cold water bath of about 60–75° F. for about 30 seconds. The nitrogen was then shut off, and the balloon was removed from the mold.

The balloons were tested by attaching the balloons to a pressurized nitrogen source in a 37° C. water bath, expanding the balloons under several predetermined pressures of nitrogen (50 psi, 100 psi, 150 psi, and burst pressure), and then measuring several dimensions and the burst pressure of the balloons. Dimensions were measured with a snap gauge.

Tables 1–18 below list certain parameters of the process utilized to make the subject balloons (hot pot temperature, cold pot temperature, weight added to mold, and nitrogen pressure). The tables also show results of the testing of the expander members. K stat was calculated as follows: (Burst pressure)–((K Stat)(Burst Pressure Standard Deviation)). Hoop stress was calculated as follows: (Balloon Burst Pressure)(Balloon Diameter)/(2)(Balloon Wall Thickness).

TABLE 1

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 250 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 1 | 0.001250 | 0.001300 | 0.001250 | .017 × .031 | 0.1120 | 0.1200 | 0.1260 | 255 |
| 2 | 0.001350 | 0.001300 | 0.001300 | .017 × .031 | 0.1120 | 0.1200 | 0.1250 | 266 |
| 3 | 0.001400 | 0.001300 | 0.001300 | .017 × .031 | 0.1125 | 0.1210 | 0.1250 | 269 |
| 4 | 0.001300 | 0.001400 | 0.001250 | .017 × .031 | 0.1120 | 0.1200 | 0.1250 | 270 |
| 5 | 0.001350 | 0.001400 | 0.001300 | .017 × .031 | 0.1130 | 0.1200 | 0.1260 | 270 |
| 6 | 0.001350 | 0.001400 | 0.001300 | .017 × .031 | | | | 252 |
| 7 | 0.001350 | 0.001400 | 0.001300 | .017 × .031 | | | | 268 |
| 8 | 0.001300 | 0.001400 | 0.001300 | .017 × .031 | | | | 270 |
| 9 | 0.001300 | 0.001350 | 0.001300 | .017 × .031 | | | | 268 |
| 10 | 0.001350 | 0.001450 | 0.001300 | .017 × .031 | | | | 280 |
| Average | 0.001330 | 0.001370 | 0.001290 | .017 × .031 | 0.11230 | 0.12020 | 0.12540 | 266.8 |
| Standard | 4.2164E – 05 | 5.37484E – 0.5 | 2.10819E – 05 | | 0.000447 | 0.000447 | 0.000548 | 7.9693859 |

Calculated K-stat (psi): 225.3353
Calculated Hoop Stress (psi): 24112

TABLE 2

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 300 GRAMS
NITROGEN 480 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 11 | 0.00190 | 0.00190 | 0.00190 | .015 × .035 | 0.1080 | 0.1180 | 0.1230 | 300 |
| 12 | 0.00180 | 0.00185 | 0.00180 | .015 × .035 | 0.1090 | 0.1180 | 0.1220 | 275 |
| 13 | 0.00170 | 0.00185 | 0.00165 | .015 × .035 | 0.1090 | 0.1180 | 0.1220 | 296 |
| 14 | 0.00180 | 0.00180 | 0.00180 | .015 × .035 | 0.1075 | 0.1170 | 0.1220 | 285 |
| 15 | 0.00190 | 0.00195 | 0.00170 | .015 × .035 | 0.1080 | 0.1180 | 0.1220 | 285 |
| 16 | 0.00180 | 0.00185 | 0.00160 | .015 × .035 | | | | 300 |
| 17 | 0.00180 | 0.00180 | 0.00180 | .015 × .035 | | | | 293 |
| 18 | 0.00190 | 0.00185 | 0.00170 | .015 × .035 | | | | 315 |
| 19 | 0.00185 | 0.00180 | 0.00165 | .015 × .035 | | | | 285 |
| 20 | 0.00170 | 0.00170 | 0.00170 | .015 × .035 | | | | 285 |
| Average | 0.001815 | 0.001835 | 0.00173 | .015 × .035 | 0.1083 | 0.1178 | 0.1222 | 291.9 |
| Standard | 7.47E – 05 | 6.687E – 0.5 | 9.18937E – 05 | | 0.000671 | 0.000447 | 0.000447 | 11.34754 |

Calculated K-stat (psi): 232.8587
Calculated Hoop Stress (psi): 28594

TABLE 3

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 250 GRAMS
NITROGEN 440 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 21 | 0.00170 | 0.00170 | 0.00170 | .017 × 0.34 | 0.110 | 0.121 | 0.125 | 293 |
| 22 | 0.00160 | 0.00160 | 0.00160 | .017 × .034 | 0.111 | 0.121 | 0.126 | 270 |
| 23 | 0.00170 | 0.00170 | 0.00170 | .017 × .034 | 0.111 | 0.120 | 0.125 | 293 |
| 24 | 0.00170 | 0.00170 | 0.00170 | .017 × .034 | 0.110 | 0.121 | 0.125 | 291 |
| 25 | 0.00160 | 0.00160 | 0.00160 | .017 × .034 | 0.110 | 0.121 | 0.125 | 293 |
| 26 | 0.00155 | 0.00150 | 0.00150 | .017 × .034 | | | | 283 |
| 27 | 0.00170 | 0.00170 | 0.00170 | .017 × .034 | | | | 293 |
| 28 | 0.00160 | 0.00160 | 0.00160 | .017 × .034 | | | | 293 |
| 29 | 0.00170 | 0.00170 | 0.00170 | .017 × .034 | | | | 287 |
| 30 | 0.00170 | 0.00170 | 0.00170 | .017 × .034 | | | | 293 |
| Average | 0.001655 | 0.001650 | 0.001650 | .017 × .034 | 0.11040 | 0.12060 | 0.12520 | 288.9 |
| Standard | 5.99E − 05 | 7.071E − 0.5 | 7.07107E − 05 | | 0.000548 | 0.000548 | 0.000447 | 7.460265 |

Calculated K-stat (psi): 250.0842
Calculated Hoop Stress (psi): 21052

TABLE 4

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 300 GRAMS
NITROGEN 320 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 31 | 0.00170 | 0.00140 | 0.00140 | .020 × 0.32 | 0.117 | 0.123 | 0.128 | 293 |
| 32 | 0.00140 | 0.00140 | 0.00140 | .020 × .032 | 0.117 | 0.123 | 0.129 | 249 |
| 33 | 0.00125 | 0.00125 | 0.00120 | .020 × .032 | 0.117 | 0.123 | 0.129 | 253 |
| 34 | 0.00135 | 0.00130 | 0.00120 | .020 × .032 | 0.116 | 0.123 | 0.129 | 251 |
| 35 | 0.00130 | 0.00130 | 0.00130 | .020 × .032 | 0.116 | 0.123 | 0.128 | 253 |
| 36 | 0.00130 | 0.00140 | 0.00135 | .020 × .032 | | | | 243 |
| 37 | 0.00140 | 0.00135 | 0.00135 | .020 × .032 | | | | 223 |
| 38 | 0.00130 | 0.00130 | 0.00130 | .020 × .032 | | | | 253 |
| 39 | 0.00135 | 0.00135 | 0.00135 | .020 × .032 | | | | 223 |
| 40 | 0.00135 | 0.00135 | 0.00125 | .020 × .032 | | | | 253 |
| Average | 0.001360 | 0.00134 | 0.0013100 | .020 × .032 | 0.1166 | 0.123 | 0.1286 | 245.2 |
| Standard | 5.16E − 05 | 5.164E − 0.5 | 7.37865E − 05 | | 0.000548 | 1.86E − 09 | 0.000548 | 12.0904 |

Calculated K-stat (psi): 182.2936
Calculated Hoop Stress (psi): 22176

TABLE 5

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 350 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 41 | 0.00160 | 0.00160 | 0.00160 | .020 × 0.35 | 0.115 | 0.125 | 0.130 | 253 |
| 42 | 0.00170 | 0.00170 | 0.00170 | .020 × .035 | 0.117 | 0.125 | 0.130 | 263 |
| 43 | 0.00160 | 0.00170 | 0.00170 | .020 × .035 | 0.117 | 0.125 | 0.130 | 269 |
| 44 | 0.00140 | 0.00150 | 0.00150 | .020 × .035 | 0.118 | 0.126 | 0.131 | 253 |
| 45 | 0.00145 | 0.00155 | 0.00150 | .020 × .035 | 0.114 | 0.123 | 0.129 | 250 |
| 46 | 0.00160 | 0.00160 | 0.00160 | .020 × .035 | | | | 269 |
| 47 | 0.00150 | 0.00150 | 0.00140 | .020 × .035 | | | | 268 |
| 48 | 0.00140 | 0.00140 | 0.00140 | .020 × .035 | | | | 239 |
| 49 | 0.00150 | 0.00150 | 0.00150 | .020 × .035 | | | | 257 |
| 50 | 0.00150 | 0.00150 | 0.00150 | .020 × .035 | | | | 257 |
| Average | 0.001525 | 0.001555 | 0.001540 | .020 × .035 | 0.1162 | 0.1248 | 0.13 | 257.8 |
| Standard | 9.79E − 05 | 9.56E − 0.5 | 0.000107497 | | 0.001643 | 0.001095 | 0.000707 | 9.681598 |

Calculated K-stat (psi): 270.4266
Calculated Hoop Stress (psi): 22097

TABLE 6

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 250 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 51 | 0.00165 | 0.00165 | 0.0016 | .023 × .035 | 0.118 | 0.127 | 0.136 | 223 |
| 52 | 0.00130 | 0.00130 | 0.0013 | .023 × .035 | 0.118 | 0.130 | 0.138 | 223 |
| 53 | 0.00130 | 0.00140 | 0.0013 | .023 × .035 | 0.117 | 0.127 | 0.135 | 239 |
| 54 | 0.00140 | 0.00140 | 0.0014 | .023 × .035 | 0.118 | 0.128 | 0.136 | 239 |
| 55 | 0.00150 | 0.00160 | 0.0016 | .023 × .035 | 0.118 | 0.127 | 0.136 | 239 |
| 56 | 0.00150 | 0.00150 | 0.0015 | .023 × .035 | | | | 250 |
| 57 | 0.00140 | 0.00140 | 0.0014 | .023 × .035 | | | | 250 |
| 58 | 0.00130 | 0.00130 | 0.0013 | .023 × .035 | | | | 238 |
| 59 | 0.00130 | 0.00130 | 0.0013 | .023 × .035 | | | | 253 |
| 60 | 0.00130 | 0.00130 | 0.0013 | .023 × .035 | | | | 239 |
| Average | 0.001395 | 0.001415 | 0.0014 | .023 × .035 | 0.1178 | 0.1278 | 0.1362 | 239.3 |
| Standard | 0.000121 | 0.0001292 | 0.000124722 | | 0.000447 | 0.001304 | 0.001095 | 10.27456 |

Calculated K-stat (psi): 185.8414
Calculated Hoop Stress (psi): 21922

TABLE 7

PEBAX GRADE: 6333
BALLOON DIMENSIONS (diameter × length): 3 × 20 mm
PARAMETERS:
HOT POT: 212° F.
COLD POT: ROOM TEMP.
WEIGHT: 350 GRAMS
NITROGEN 420 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 61 | 0.00150 | 0.00150 | 0.0015 | .023 × .038 | 0.118 | 0.126 | 0.134 | 253 |
| 62 | 0.00150 | 0.00150 | 0.0015 | .023 × .038 | 0.119 | 0.126 | 0.135 | 253 |
| 63 | 0.00160 | 0.00160 | 0.0016 | .023 × .038 | 0.121 | 0.130 | 0.138 | 260 |
| 64 | 0.00160 | 0.00160 | 0.0016 | .023 × .038 | 0.120 | 0.127 | 0.138 | 245 |
| 65 | 0.00140 | 0.00140 | 0.0014 | .023 × .038 | 0.120 | 0.127 | 0.139 | 253 |
| 66 | 0.00160 | 0.00160 | 0.0015 | .023 × .038 | | | | 253 |
| 67 | 0.00160 | 0.00160 | 0.0016 | .023 × .038 | | | | 253 |
| 68 | 0.00160 | 0.00160 | 0.0016 | .023 × .038 | | | | 263 |
| 69 | 0.00170 | 0.00170 | 0.0017 | .023 × .038 | | | | 253 |
| 70 | 0.00145 | 0.00145 | 0.0015 | .023 × .038 | | | | 258 |
| Average | 0.001555 | 0.001555 | 0.00155 | .023 × .038 | 0.1196 | 0.1272 | 0.1368 | 254.4 |
| Standard | 8.96E − 05 | 8.96E − 05 | 8.49837E − 05 | | 0.00114 | 0.001643 | 0.002168 | 4.926121 |

Calculated K-stat (psi): 228.7694
Calculated Hoop Stress (psi): 20810

TABLE 8

PEBAX GRADE: 7033
BALLOON DIMENSIONS (diameter × length): 3 × 20 mm
PARAMETERS:
HOT POT: 212° F.
COLD POT: ROOM TEMP.
WEIGHT: 250 GRAMS
NITROGEN 460 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 71 | 0.00145 | 0.00155 | 0.00155 | .017 × .034 | 0.1110 | 0.119 | 0.123 | 305 |
| 72 | 0.00150 | 0.00150 | 0.00150 | .017 × .034 | 0.1100 | 0.120 | 0.124 | 307 |
| 73 | 0.00145 | 0.00150 | 0.00155 | .017 × .034 | 0.1100 | 0.118 | 0.123 | 293 |
| 74 | 0.00140 | 0.00150 | 0.00150 | .017 × .034 | 0.1100 | 0.120 | 0.123 | 323 |
| 75 | 0.00145 | 0.00155 | 0.00150 | .017 × .034 | 0.1100 | 0.118 | 0.124 | 309 |
| 76 | 0.00150 | 0.00150 | 0.00150 | .017 × .034 | | | | 295 |
| 77 | 0.00150 | 0.00140 | 0.00145 | .017 × .034 | | | | 323 |
| 78 | 0.00140 | 0.00140 | 0.00140 | .017 × .034 | | | | 293 |
| 79 | 0.00150 | 0.00150 | 0.00150 | .017 × .034 | | | | 320 |
| 80 | 0.00150 | 0.00150 | 0.00150 | .017 × .034 | | | | 303 |
| Average | 0.001475 | 0.00149 | 0.001495 | .017 × .034 | 0.1102 | 0.119 | 0.1234 | 307.1 |
| Standard | 5.89E − 05 | 5.164E − 05 | 4.37798E − 05 | | 0.000447 | 0.001 | 0.000548 | 11.74214 |

Calculated K-stat (psi): 246.0057
Calculated Hoop Stress (psi): 24776

TABLE 9

PEBAX GRADE: 7033
BALLOON DIMENSIONS (diameter × length): 3 × 20 mm
PARAMETERS:
HOT POT: 205° F.
COLD POT: ROOM TEMP.
WEIGHT: 250 GRAMS
NITROGEN 380 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 81 | 0.00115 | 0.00115 | 0.00115 | .020 × .032 | 0.114 | 0.120 | 0.125 | 270 |
| 82 | 0.00125 | 0.00125 | 0.00115 | .020 × .032 | 0.113 | 0.120 | 0.125 | 270 |
| 83 | 0.00130 | 0.00139 | 0.00120 | .020 × .032 | 0.114 | 0.120 | 0.125 | 270 |
| 84 | 0.00120 | 0.00120 | 0.00110 | .020 × .032 | 0.113 | 0.120 | 0.125 | 270 |
| 85 | 0.00120 | 0.00120 | 0.00115 | .020 × .032 | 0.115 | 0.121 | 0.126 | 270 |
| 86 | 0.00115 | 0.00115 | 0.00110 | .020 × .032 | | | | 250 |
| 87 | 0.00115 | 0.00120 | 0.00110 | .020 × .032 | | | | 271 |
| 88 | 0.00115 | 0.00120 | 0.00115 | .020 × .032 | | | | 270 |
| 89 | 0.00125 | 0.00120 | 0.00120 | .020 × .032 | | | | 270 |
| 90 | 0.00120 | 0.00115 | 0.00115 | .020 × .032 | | | | 269 |
| Average | 0.0012 | 0.0012 | 0.001145 | .020 × .032 | 0.1138 | 0.1202 | 0.1252 | 268 |
| Standard | 5.27E − 05 | 4.714E − 05 | 3.68932E − 05 | | 0.000837 | 0.000447 | 0.000447 | 6.342099 |

Calculated K-stat (psi): 235.0021
Calculated Hoop Stress (psi): 26844

TABLE 10

PEBAX GRADE: 7033
BALLOON DIMENSIONS (diameter × length): 3 × 20 mm
PARAMETERS:
HOT POT: 212° F.
COLD POT: ROOM TEMP.
WEIGHT: 250 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 91 | 0.00130 | 0.00135 | 0.00140 | .020 × .035 | 0.109 | 0.119 | 0.125 | 295 |
| 92 | 0.00130 | 0.00135 | 0.00140 | .020 × .035 | 0.115 | 0.124 | 0.128 | 300 |
| 93 | 0.00130 | 0.00135 | 0.00130 | .020 × .035 | 0.115 | 0.122 | 0.127 | 289 |
| 94 | 0.00130 | 0.00135 | 0.00130 | .020 × .035 | 0.113 | 0.124 | 0.130 | 298 |
| 95 | 0.00130 | 0.00140 | 0.00130 | .020 × .035 | 0.115 | 0.124 | 0.128 | 283 |
| 96 | 0.00135 | 0.00135 | 0.00135 | .020 × .035 | | | | 297 |
| 97 | 0.00140 | 0.00140 | 0.00140 | .020 × .035 | | | | 297 |
| 98 | 0.00140 | 0.00140 | 0.00140 | .020 × .035 | | | | 297 |
| 99 | 0.00140 | 0.00130 | 0.00140 | .020 × .035 | | | | 290 |
| 100 | 0.00130 | 0.00130 | 0.00130 | .020 × .035 | | | | 290 |
| Average | 0.001335 | 0.001355 | 0.001355 | .020 × .035 | 0.1134 | 0.1226 | 0.1276 | 293.6 |
| Standard | 4.74E − 05 | 3.689E − 05 | 4.97214E − 05 | | 0.002608 | 0.002191 | 0.001817 | 5.337498 |

Calculated K-stat (psi): 265.829
Calculated Hoop Stress (psi): 26962

TABLE 11

PEBAX GRADE: 7033
BALLOON DIMENSIONS (diameter × length): 3 × 20 mm
PARAMETERS:
HOT POT: 210° F.
COLD POT: ROOM TEMP.
WEIGHT: 350 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 101 | 0.0014 | 0.0014 | 0.00140 | .023 × .035 | 0.115 | 0.121 | 0.127 | 298 |
| 102 | 0.0013 | 0.0013 | 0.00125 | .023 × .035 | 0.117 | 0.126 | 0.134 | 253 |
| 103 | 0.0013 | 0.0013 | 0.00120 | .023 × .035 | 0.117 | 0.126 | 0.131 | 275 |
| 104 | 0.0013 | 0.0013 | 0.00130 | .023 × .035 | 0.118 | 0.126 | 0.132 | 238 |
| 105 | 0.0013 | 0.0013 | 0.00140 | .023 × .035 | 0.116 | 0.127 | 0.133 | 281 |
| 106 | 0.0013 | 0.0013 | 0.00140 | .023 × .035 | | | | 280 |
| 107 | 0.0013 | 0.0013 | 0.00140 | .023 × .035 | | | | 269 |
| 108 | 0.0012 | 0.0012 | 0.00130 | .023 × .035 | | | | 280 |
| 109 | 0.0012 | 0.0012 | 0.00125 | .023 × .035 | | | | 283 |
| 110 | 0.0012 | 0.0012 | 0.00125 | .023 × .035 | | | | 283 |
| Average | 0.00128 | 0.00128 | 0.001315 | .023 × .035 | 0.1166 | 0.1252 | 0.1314 | 274 |
| Standard | 6.32E − 05 | 6.325E − 05 | 7.83511E − 05 | | 0.00114 | 0.002387 | 0.002702 | 17.06849 |

Calculated K-stat (psi): 185.1926
Calculated Hoop Stress (psi): 26800

TABLE 12

PEBAX GRADE: 7033
BALLOON DIMENSIONS (diameter × length): 3 × 20 mm
PARAMETERS:
HOT POT: 210° F.
COLD POT: ROOM TEMP.
WEIGHT: 350 GRAMS
NITROGEN 420 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 111 | 0.00150 | 0.0015 | 0.0014 | .023 × .038 | 0.119 | 0.125 | 0.130 | 310 |
| 112 | 0.00160 | 0.0016 | 0.0016 | .023 × .038 | 0.118 | 0.125 | 0.130 | 300 |
| 113 | 0.00160 | 0.0016 | 0.0016 | .023 × .038 | 0.118 | 0.125 | 0.130 | 293 |
| 114 | 0.00150 | 0.0015 | 0.0015 | .023 × .038 | 0.118 | 0.126 | 0.131 | 283 |
| 115 | 0.00150 | 0.0015 | 0.0015 | .023 × .038 | 0.119 | 0.125 | 0.130 | 280 |
| 116 | 0.00150 | 0.0016 | 0.0015 | .023 × .038 | | | | 300 |
| 117 | 0.00145 | 0.0015 | 0.0015 | .023 × .038 | | | | 310 |
| 118 | 0.00160 | 0.0016 | 0.0016 | .023 × .038 | | | | 298 |
| 119 | 0.00150 | 0.0015 | 0.0015 | .023 × .038 | | | | 298 |
| 120 | 0.00145 | 0.0015 | 0.0015 | .023 × .038 | | | | 313 |
| Average | 0.00152 | 0.00154 | 0.00152 | .023 × .038 | 0.1184 | 0.1252 | 0.1302 | 298.5 |
| Standard | 5.87E − 05 | 5.164E − 05 | 6.32456E − 05 | | 0.000548 | 0.000447 | 0.000447 | 11.01766 |

Calculated K-stat (psi): 241.1751
Calculated Hoop Stress (psi): 24586

TABLE 13

PEBAX GRADE: 7233
BALLOON DIMENSIONS (diameter × length): 3 × 20 mm
PARAMETERS:
HOT POT: 212° F.
COLD POT: ROOM TEMP.
WEIGHT: 300 GRAMS
NITROGEN 460 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 121 | 0.00110 | 0.00120 | 0.00110 | .017 × .031 | 0.108 | 0.116 | 0.120 | 330 |
| 122 | 0.00120 | 0.00135 | 0.00120 | 017 × 031 | 0.106 | 0.115 | 0.119 | 345 |
| 123 | 0.00130 | 0.00140 | 0.00135 | 017 × 031 | 0.106 | 0.116 | 0.120 | 300 |
| 124 | 0.00130 | 0.00130 | 0.00120 | 017 × 031 | 0.106 | 0.116 | 0.120 | 345 |
| 125 | 0.00130 | 0.00130 | 0.00125 | 017 × 031 | 0.108 | 0.116 | 0.120 | 360 |
| 126 | 0.00135 | 0.00130 | 0.00120 | 017 × 031 | | | | 345 |
| 127 | 0.00145 | 0.00130 | 0.00130 | 017 × 031 | | | | 375 |
| 128 | 0.00130 | 0.00130 | 0.00130 | 017 × 031 | | | | 330 |
| 129 | 0.00145 | 0.00130 | 0.00140 | 017 × 031 | | | | 300 |
| 130 | 0.00140 | 0.00140 | 0.00135 | 017 × 031 | | | | 345 |
| Average | 0.001315 | 0.001315 | 0.001265 | .017 × .031 | 0.10680 | 0.11580 | 0.11980 | 337.5 |
| Standard | 0.000108 | 5.798E − 05 | 9.14391 E − 05 | | 0.001095 | 0.000447 | 0.000447 | 23.71708 |

Calculated K-stat (psi): 214.1
Calculated Hoop Stress (psi): 29720

TABLE 14

PEBAX GRADE: 7233
BALLOON DIMENSIONS (diameter × length): 3 × 20 mm
PARAMETERS:
HOT POT: 212° F.
COLD POT: ROOM TEMP.
WEIGHT: 350 GRAMS
NITROGEN 500 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 131 | 0.00150 | 0.00150 | 0.0015 | .017 × .034 | 0.11 | 0.116 | 0.121 | 303 |
| 132 | 0.00160 | 0.00160 | 0.0016 | .017 × .034 | 0.11 | 0.116 | 0.121. | 280 |
| 133 | 0.00160 | 0.00160 | 0.0016 | .017 × .034 | 0.11 | 0.116 | 0.121 | 353 |
| 134 | 0.00155 | 0.00155 | 0.0015 | .017 × .034 | 0.11 | 0.117 | 0.120 | 340 |
| 135 | 0.00160 | 0.00160 | 0.0016 | .017 × .034 | 0.11 | 0.116 | 0.121 | 348 |
| 136 | 0.00160 | 0.00160 | 0.0016 | .017 × .034 | | | | 338 |
| 137 | 0.00160 | 0.00160 | 0.0016 | .017 × .034 | | | | 350 |
| 138 | 0.00170 | 0.00170 | 0.0017 | .017 × .034 | | | | 369 |
| 139 | 0.00170 | 0.00170 | 0.0017 | .017 × .034 | | | | 318 |
| 140 | 0.00170 | 0.00170 | 0.0017 | .017 × .034 | | | | 353 |
| Average | 0.001615 | 0.001615 | 0.00161 | .017 × .034 | 0.11 | 0.1162 | 0.1208 | 335.2 |
| Standard | 6.69E − 05 | 6.687E − 05 | 7.37865E − 05 | | 0.0 | 0.000447 | 0.000447 | 27.01769 |

Calculated K-stat (psi): 194.627
Calculated Hoop Stress (psi): 24117

TABLE 15

PEBAX GRADE: 7233
BALLOON DIMENSIONS (diameter × length): 3 × 20 mm
PARAMETERS:
HOT POT: 210° F.
COLD POT: ROOM TEMP.
WEIGHT: 350 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 141 | 0.00140 | 0.00140 | 0.00140 | .020 × .035 | 0.112 | 0.120 | 0.125 | 359 |
| 142 | 0.00140 | 0.00150 | 0.00150 | .020 × .035 | 0.112 | 0.118 | 0.125 | 325 |
| 143 | 0.00140 | 0.00150 | 0.00150 | .020 × .035 | 0.113 | 0.118 | 0.123 | 329 |
| 144 | 0.00150 | 0.00150 | 0.00150 | .020 × .035 | 0.111 | 0.120 | 0.123 | 359 |
| 145 | 0.00150 | 0.00150 | 0.00150 | .020 × .035 | 0.113 | 0.120 | 0.124 | 350 |
| 146 | 0.00145 | 0.00150 | 0.00150 | .020 × .035 | | | | 330 |
| 147 | 0.00150 | 0.00160 | 0.00160 | .020 × .035 | | | | 343 |
| 148 | 0.00140 | 0.00130 | 0.00130 | .020 × .035 | | | | 353 |
| 148 | 0.00155 | 0.00155 | 0.00155 | .020 × .035 | | | | 309 |
| 150 | 0.00150 | 0.00150 | 0.00150 | .020 × .035 | | | | 343 |
| Average | 0.00146 | 0.001485 | 0.001485 | .020 × .035 | 0.1122 | 0.1192 | 0.124 | 340 |
| Standard | 5.68E − 05 | 8.182E − 05 | 8.18196E − 05 | | 0.000837 | 0.001095 | 0.001 | 16.38427 |

Calculated K-stat (psi): 254.7526
Calculated Hoop Stress (psi): 27018

TABLE 16

PEBAX GRADE: 7233
BALLOON DIMENSIONS (diameter × length): 3 × 20 mm
PARAMETERS:
HOT POT: 205° F.
COLD POT: ROOM TEMP.
WEIGHT: 320 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 151 | 0.0013 | 0.00125 | 0.001250 | .020 × .032 | 0.114 | 0.119 | 0.123 | 357 |
| 152 | 0.0013 | 0.00135 | 0.001300 | .020 × .032 | 0.113 | 0.119 | 0.123 | 359 |
| 153 | 0.0013 | 0.00120 | 0.001200 | .020 × .032 | 0.113 | 0.119 | 0.123 | 359 |
| 154 | 0.0012 | 0.00125 | 0.001200 | .020 × .032 | 0.112 | 0.119 | 0.123 | 369 |
| 155 | 0.0013 | 0.00120 | 0.001200 | .020 × .032 | 0.113 | 0.118 | 0.123 | 353 |
| 156 | 0.0012 | 0.00125 | 0.001250 | .020 × .032 | | | | 343 |
| 157 | 0.0014 | 0.00135 | 0.001350 | .020 × .032 | | | | 359 |
| 158 | 0.0013 | 0.00130 | 0.001300 | .020 × .032 | | | | 359 |
| 159 | 0.0012 | 0.00120 | 0.001150 | .020 × .032 | | | | 361 |
| 160 | 0.0013 | 0.00130 | 0.001250 | .020 × .032 | | | | 313 |
| Average | 0.00126 | 0.001265 | 0.001245 | .020 × .032 | 0.113 | 0.1188 | 0.12300 | 353.2 |
| Standard | 4.9721E − 05 | 5.798E − 05 | 5.98609E − 05 | | 0.000707 | 0.000447 | 1.86E − 09 | 15.56206 |

Calculated K-stat (psi): 272.2306
Calculated Hoop Stress (psi): 33342

TABLE 17

PEBAX GRADE: 7233
BALLOON DIMENSIONS (diameter × length): 3 × 20 mm
PARAMETERS:
HOT POT: 210° F.
COLD POT: ROOM TEMP.
WEIGHT: 380 GRAMS
NITROGEN 400 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 161 | 0.00140 | 0.00140 | 0.00140 | .023 × .035 | 0.116 | 0.122 | 0.126 | 329 |
| 162 | 0.00150 | 0.00150 | 0.00140 | .023 × .035 | 0.116 | 0.122 | 0.127 | 329 |
| 163 | 0.00140 | 0.00140 | 0.00150 | .023 × .035 | 0.116 | 0.123 | 0.128 | 330 |
| 164 | 0.00140 | 0.00140 | 0.00150 | .023 × .035 | 0.116 | 0.123 | 0.128 | 270 |
| 165 | 0.00135 | 0.00135 | 0.00135 | .023 × .035 | 0.117 | 0.124 | 0.129 | 343 |
| 166 | 0.00140 | 0.00140 | 0.00140 | .023 × .035 | | | | 300 |
| 167 | 0.00140 | 0.00140 | 0.00150 | .023 × .035 | | | | 345 |
| 168 | 0.00140 | 0.00140 | 0.00140 | .023 × .035 | | | | 329 |
| 169 | 0.00140 | 0.00140 | 0.00140 | .023 × .035 | | | | 330 |
| 170 | 0.00140 | 0.00140 | 0.00140 | .023 × .035 | | | | 330 |
| Average | 0.001405 | 0.001405 | 0.001425 | .023 × .035 | 0.1162 | 0.1228 | 0.1276 | 323.5 |
| Standard | 3.69E − 05 | 3.689E − 05 | 5.40062E − 05 | | 0.000447 | 0.000837 | 0.00114 | 22.29723 |

Calculated K-stat (psi): 207.4875
Calculated Hoop Stress (psi): 28274

TABLE 18

PEBAX GRADE: 7233
BALLOON DIMENSIONS (diameter × length): 3 × 20 mm
PARAMETERS:
HOT POT:
COLD POT: ROOM TEMP.
WEIGHT: 350 GRAMS
NITROGEN 420 PSI

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 171 | 0.00160 | 0.00160 | 0.001550 | .023 × .038 | 0.114 | 0.120 | 0.126 | 375 |
| 172 | 0.00160 | 0.00160 | 0.001600 | .023 × .038 | 0.115 | 0.122 | 0.126 | 300 |
| 173 | 0.00165 | 0.00160 | 0.001500 | .023 × .038 | 0.119 | 0.125 | 0.128 | 298 |
| 174 | 0.00160 | 0.00165 | 0.001600 | .023 × .038 | 0.116 | 0.122 | 0.127 | 328 |
| 175 | 0.00160 | 0.00160 | 0.001600 | .023 × .038 | 0.116 | 0.123 | 0.126 | 343 |
| 176 | 0.00170 | 0.00170 | 0.001700 | .023 × .038 | | | | 370 |
| 177 | 0.00160 | 0.00170 | 0.001600 | .023 × .038 | | | | 370 |
| 178 | 0.00170 | 0.00170 | 0.001700 | .023 × .038 | | | | 355 |
| 179 | 0.00165 | 0.00170 | 0.001650 | .023 × .038 | | | | 358 |
| 180 | 0.00170 | 0.00170 | 0.001700 | .023 × .038 | | | | 373 |
| Average | 0.00164 | 0.001655 | 0.00162 | .023 × .038 | 0.116 | 0.1224 | 0.1266 | 347 |
| Standard | 4.59E − 05 | 4.972E − 05 | 6.74949E − 05 | | 0.001871 | 0.001817 | 0.000894 | 29.23088 |

Calculated K-stat (psi): 194.9117
Calculated Hoop Stress (psi): 25898

Examples 181–206

26 balloons were made according to the process described for Examples 1–180, except that the mold apparatus did not utilize weights 22 separately, but rather incorporated a preselected weight into handle 20.

The balloons were tested to measure distension and balloon burst strength. Distension is defined as the ratio of two balloon diameters. In this test, a balloon was inflated to a series of pressures. The diameter was measured at each pressure. The distension is the ratio of the diameter at the lowest pressure to the diameter at the highest pressure. Inflation was performed at 1 bar increments up to burst pressure.

To test the balloons, the balloons were first placed in temperature controlled water bath, and warmed for a minimum of 1 minute in water. The balloons were then attached to a pneumatic inflation/deflation device. A vacuum was created. Starting with a 4 bar pressure for 20 seconds, the balloon diameter and length were measured. The balloons were deflated, and the measurements were recorded. Increasing the pressure by 1 bar, the balloon diameters and lengths were measured. This procedure was repeated until the balloons bursted. The burst pressure and the type of burst profile were recorded.

Tables 19–21 below show the results of the testing of the expander members.

TABLE 19

PEBAX GRADE 7233
Tubing Dimensions (ID × OD): 0.48 × 0.81 mm
Balloon Dimensions (OD × length): 3.0 × 20 mm
Diameter Form: 3.00 mm DIAMETER (mm)
Balloon Number

| atm | 181 | 182 | 183 | 184 | 185 | 186 | 187 | 188 | 189 | 190 | Average |
|---|---|---|---|---|---|---|---|---|---|---|---|
| 4  | 2.57 | 2.60 | 3 | 2.60 | 2.57 | 2.55 | 2.54 | 2.54 | 2.61 | 2.57 | 2.58 |
| 6  | 2.79 | 2.81 | 3 | 2.81 | 2.79 | 2.79 | 2.70 | 2.75 | 2.78 | 2.80 | 2.78 |
| 8  | 2.91 | 2.94 | 3 | 2.93 | 2.93 | 2.95 | 2.89 | 2.88 | 2.93 | 2.93 | 2.92 |
| 10 | 3.01 | 3.01 | 3 | 3.02 | 3.02 | 3.01 | 2.99 | 3.00 | 3.00 | 3.02 | 3.01 |
| 12 | 3.06 | 3.07 | 3 | 3.08 | 3.09 | 3.08 | 3.03 | 3.05 | 3.06 | 3.07 | 3.07 |
| 14 | 3.12 | 3.14 | 3 | 3.13 | 3.12 | 3.12 | 3.09 | 3.11 | 3.12 | 3.12 | 3.12 |
| 16 | 3.17 | 3.17 | 3 | 3.17 | 3.18 | 3.17 | 3.14 | 3.16 | 3.16 | 3.18 | 3.17 |
| 18 | 3.23 | 3.24 | 3 | 3.25 | 3.24 | 3.23 | 3.21 | 3.22 | 3.23 | 3.23 | 3.23 |

Average burst pressure 21.1 atm
Minimum burst pressure 20.0 atm
Maximum burst pressure 22.0 atm

TABLE 20

PEBAX GRADE 7233
Tubing Dimensions (ID × OD): 0.48 × 0.82 mm
Balloon Dimensions (OD × length): 3.0 × 20 mm
Diameter Form: 3.25 mm DIAMETER (mm)
Balloon Number

| atm | 191 | 192 | 193 | 194 | 195 | 196 | 197 | 198 | Average |
|---|---|---|---|---|---|---|---|---|---|
| 4  | 2.73 | 2.74 | 2.66 | 2.71 | 2.69 | 2.71 | 2.70 | 2.77 | 2.71 |
| 6  | 2.97 | 2.93 | 2.89 | 2.92 | 2.92 | 2.94 | 2.97 | 3.01 | 2.94 |
| 8  | 3.12 | 3.06 | 3.03 | 3.08 | 3.06 | 3.07 | 3.08 | 3.12 | 3.08 |
| 10 | 3.18 | 3.12 | 3.15 | 3.16 | 3.12 | 3.17 | 3.18 | 3.19 | 3.16 |
| 12 | 3.23 | 3.20 | 3.22 | 3.23 | 3.19 | 3.23 | 3.23 | 3.26 | 3.22 |
| 14 | 3.30 | 3.27 | 3.27 | 3.27 | 3.25 | 3.28 | 3.28 | 3.33 | 3.28 |
| 16 | 3.33 | 3.31 | 3.31 | 3.30 | 3.29 | 3.32 | 3.32 | 3.36 | 3.32 |
| 18 | 3.39 | 3.33 | 3.37 | 3.37 | 3.36 | 3.40 | 3.39 | 3.43 | 3.38 |

Average burst pressure 21.4 atm
Minimum burst pressure 20.0 atm
Maximum burst pressure 22.0 atm

TABLE 21

PEBAX GRADE 7233
Tubing Dimensions (ID × OD): 0.65 × 0.90 mm
Balloon Dimensions (OD × length): 3.0 × 20 mm
Diameter Form: 3.25 mm DIAMETER (mm)
Balloon Number

| atm | 199 | 200 | 201 | 202 | 203 | 204 | 205 | 206 | Average |
|---|---|---|---|---|---|---|---|---|---|
| 4  | 2.91 | 2.92 | 2.94 | 2.91 | 2.87 | 2.85 | 2.93 | 2.99 | 2.92 |
| 6  | 3.17 | 3.15 | 3.16 | 3.13 | 3.14 | 3.10 | 3.17 | 3.19 | 3.15 |
| 8  | 3.28 | 3.32 | 3.29 | 3.29 | 3.28 | 3.25 | 3.31 | 3.33 | 3.29 |
| 10 | 3.40 | 3.44 | 3.41 | 3.39 | 3.40 | 3.36 | 3.42 | 3.44 | 3.41 |
| 12 | 3.52 | 3.52 | 3.49 | 3.52 | 3.51 | 3.48 | 3.52 | 3.53 | 3.51 |
| 14 | 3.66 | 3.65 | 3.64 | 3.65 | 3.65 | 3.62 | 3.66 | 3.66 | 3.65 |
| 16 | 3.79 | 3.79 | 3.82 | 3.83 | 3.80 | 3.78 | 3.82 | 3.85 | 3.81 |
| 18 | 4.05 | — | — | — | 4.06 | 4.08 | 4.05 | 4.17 | 4.08 |

Average burst pressure 19.3 atm
Minimum burst pressure 18.0 atm
Maximum burse pressure 20.0 atm

Examples 207–236

30 balloons were made according to the procedure described above for Examples 1–180, except that parisons had inside diameters of about 0.025 inches and wall thicknesses of about 0.0065 inches.

The balloons were tested according to the procedure described above for Examples 1–180, except that outside diameters were measured at 1 atm increments from 4–16 atms, and then the balloons were burst.

Tables 22–28 below list certain parameters (PEBAX grade, dimensions, cone angle, rated burst, and hold time representing the total amount of time that the mold was held in the water). The tables also show results of the testing of the expander members.

TABLE 22

BALLOON COMPLIANCE

Pebax Grade: 7233
Dimensions (dia. × lgt.): 3.0 × 20 mm
Cone Angle: 10 degrees
Rated Burst: 176 psi
Hold (Secs.): 15

| Pressure | | DIAMETER (inches) Balloon Number | | | | |
|---|---|---|---|---|---|---|
| atm | psi | 207 | 208 | 209 | 210 | 211 |
| 4 | 58.8 | .111 | .111 | .112 | .112 | .112 |
| 5 | 73.5 | .113 | .114 | .115 | .114 | .115 |
| 6 | 88.2 | .116 | .116 | .117 | .116 | .117 |
| 7 | 102.5 | .118 | .117 | .118 | .117 | .118 |
| 8 | 117.6 | .119 | .119 | .119 | .118 | .119 |
| 9 | 132.3 | .120 | .120 | .120 | .119 | .120 |
| 10 | 147.0 | .122 | .121 | .121 | .120 | .121 |
| 11 | 161.7 | .122 | .122 | .122 | .121 | .122 |
| 12 | 176.4 | .123 | .123 | .123 | .122 | .123 |
| 13 | 191.1 | .124 | .124 | .124 | .123 | .124 |
| 14 | 205.8 | .125 | .125 | .125 | .124 | .125 |
| 15 | 220.5 | .126 | .126 | .125 | .125 | .126 |
| 16 | 235.2 | .127 | .127 | .126 | .125 | .127 |
| Burst Pressure (psi) | | 278 | 249 | 278 | 307 | 291 |
| Direction of Burst | | Axial | Axial | Axial | Axial | Axial |

TABLE 23

BALLOON COMPLIANCE

Pebax Grade: 7233
Dimensions (dia. × lgt.): 3.0 × 20 mm
Cone Angle: 10 degrees
Rated Burst: 176 psi
Hold (Secs.): 15

| Pressure | | DIAMETER (inches) Balloon Number | | | | |
|---|---|---|---|---|---|---|
| atm | psi | 212 | 213 | 214 | 215 | 216 |
| 4 | 58.8 | .113 | .113 | .111 | .112 | .111 |
| 5 | 73.5 | .115 | .115 | .114 | .114 | .114 |
| 6 | 88.2 | .117 | .117 | .116 | .116 | .116 |
| 7 | 102.5 | .118 | .118 | .118 | .118 | .117 |
| 8 | 117.6 | .119 | .119 | .119 | .119 | .118 |
| 9 | 132.3 | .120 | .120 | .120 | .120 | .120 |
| 10 | 147.0 | .121 | .121 | .121 | .121 | .120 |
| 11 | 161.7 | .122 | .122 | .122 | .122 | .121 |
| 12 | 176.4 | .123 | .123 | .123 | .123 | .122 |
| 13 | 191.1 | .124 | .124 | .124 | .124 | .123 |
| 14 | 205.8 | .125 | .125 | .125 | .125 | .124 |
| 15 | 220.5 | .126 | .126 | .126 | .126 | .125 |
| 16 | 235.2 | .127 | .127 | .127 | .127 | .126 |
| Burst Pressure (psi) | | 266 | 264 | 280 | 290 | 280 |
| Direction of Burst | | Axial | Axial | Axial | Axial | Axial |

TABLE 24

BALLOON COMPLIANCE

PEBAX Grade: 7233
Dimensions (dia. × lgt.): 3.0 × 20 mm
Cone Angle: 10 degrees
Rated Burst: 176 psi
Hold (Secs.): 15

| Pressure | | DIAMETER (inches) Balloon Number | | | | |
|---|---|---|---|---|---|---|
| atm | psi | 217 | 218 | 219 | 220 | 221 |
| 4 | 58.8 | .109 | .110 | .110 | .109 | .109 |
| 5 | 73.5 | .112 | .114 | .114 | .112 | .114 |
| 6 | 88.2 | .114 | .116 | .115 | .114 | .116 |
| 7 | 102.5 | .116 | .117 | .117 | .116 | .118 |
| 8 | 117.6 | .117 | .119 | .118 | .117 | .119 |
| 9 | 132.3 | .119 | .119 | .120 | .119 | .120 |
| 10 | 147.0 | .120 | .120 | .121 | .120 | .121 |
| 11 | 161.7 | .121 | .121 | .122 | .121 | .122 |
| 12 | 176.4 | .122 | .122 | .123 | .122 | .123 |
| 13 | 191.1 | .123 | .124 | .124 | .123 | .124 |
| 14 | 205.8 | .124 | .125 | .125 | .124 | .125 |
| 15 | 220.5 | .125 | .126 | .126 | .125 | .126 |
| 16 | 235.2 | .125 | .127 | .127 | .126 | .127 |
| Burst Pressure (psi) | | 290 | 250 | 250 | 250 | 250 |
| Direction of Burst | | Axial | Axial | Axial | Axial | Axial |

TABLE 25

BALLOON COMPLIANCE

PEBAX Grade: 7233
Dimensions (dia. × lgt.): 3.0 × 20 mm
Cone Angle: 10 degrees
Rated Burst: 176 psi
Hold (Secs.): 15

| Pressure | | DIAMETER (inches) Balloon Number | | | | |
|---|---|---|---|---|---|---|
| atm | psi | 222 | 223 | 224 | 225 | 226 |
| 4 | 58.8 | .108 | .111 | .111 | .111 | .110 |
| 5 | 73.5 | .110 | .114 | .114 | .113 | .113 |
| 6 | 88.2 | .112 | .116 | .116 | .115 | .115 |
| 7 | 102.5 | .114 | .118 | .117 | .117 | .117 |
| 8 | 11.6 | .116 | .119 | .118 | .118 | .118 |
| 9 | 132.3 | .117 | .120 | .120 | .119 | .119 |
| 10 | 147.0 | .119 | .121 | .121 | .120 | .120 |
| 11 | 161.7 | .120 | .122 | .122 | .121 | .121 |
| 12 | 176.4 | .121 | .123 | .123 | .122 | .122 |
| 13 | 191.1 | .122 | .124 | .124 | .123 | .123 |
| 14 | 205.8 | .123 | .125 | .125 | .124 | .124 |
| 15 | 220.5 | .124 | .126 | .126 | .125 | .125 |
| 16 | 235.2 | .125 | .127 | .127 | .126 | .126 |
| Burst Pressure (psi) | | 264 | 280 | 260 | 280 | 290 |
| Direction of Burst | | Axial | Axial | Axial | Axial | Axial |

TABLE 26

BALLOON COMPLIANCE

PEBAX Grade: 7233
Dimensions (dia. × lgt.): 3.0 × 20 mm
Cone Angle: 10 degrees
Rated Burst: 176 psi
Hold (Secs.): 15

| Pressure | | DIAMETER (inches) Balloon Number | | | | |
|---|---|---|---|---|---|---|
| atm | psi | 227 | 228 | 229 | 230 | 231 |
| 4 | 58.8 | .111 | .111 | .110 | .111 | .110 |
| 5 | 73.5 | .113 | .114 | .113 | .113 | .113 |

TABLE 26-continued

BALLOON COMPLIANCE

PEBAX Grade: 7233  
Dimensions (dia. × lgt.): 3.0 × 20 mm  
Cone Angle: 10 degrees  
Rated Burst: 176 psi  
Hold (Secs.) 15

| Pressure | | DIAMETER (inches) Balloon Number | | | | |
|---|---|---|---|---|---|---|
| atm | psi | 227 | 228 | 229 | 230 | 231 |
| 6 | 88.2 | .115 | .116 | .114 | .115 | .115 |
| 7 | 102.5 | .117 | .118 | .116 | .117 | .117 |
| 8 | 117.6 | .119 | .119 | .118 | .118 | .118 |
| 9 | 132.3 | .120 | .120 | .119 | .119 | .119 |
| 10 | 147.0 | .121 | .121 | .120 | .120 | .120 |
| 11 | 161.7 | .122 | .122 | .121 | .121 | .121 |
| 12 | 176.4 | .123 | .123 | .123 | .122 | .122 |
| 13 | 191.1 | .123 | .124 | .124 | .123 | .123 |
| 14 | 205.8 | .124 | .125 | .125 | .124 | .124 |
| 15 | 220.5 | .125 | .126 | .126 | .125 | .125 |
| 16 | 235.2 | .126 | .127 | .127 | .126 | .126 |
| Burst Pressure (psi) | | 278 | 280 | 265 | 260 | 260 |
| Direction of Burst | | Axial | Axial | Axial | Axial | Axial |

TABLE 27

BALLOON COMPLIANCE

PEBAX Grade: 7233  
Dimensions (dia. × lgt.): 3.0 × 20 mm  
Cone Angle: 10 degrees  
Rated Burst: 176 psi  
Hold (Secs.) 15

| Pressure | | DIAMETER (inches) Balloon Number | | | | |
|---|---|---|---|---|---|---|
| atm | psi | 232 | 233 | 234 | 235 | 236 |
| 4 | 58.8 | .111 | .111 | .110 | .111 | .112 |
| 5 | 73.5 | .114 | .114 | .113 | .114 | .115 |
| 6 | 88.2 | .116 | .116 | .116 | .116 | .1165 |
| 7 | 102.5 | .117 | .117 | .117 | .117 | .118 |
| 8 | 117.6 | .119 | .190 | .118 | .1185 | .119 |
| 9 | 132.3 | .120 | .120 | .119 | .120 | .120 |
| 10 | 147.0 | .121 | .121 | .1205 | .121 | .121 |
| 11 | 161.7 | .122 | .122 | .122 | .122 | .122 |
| 12 | 176.4 | .1225 | .123 | .123 | .123 | .123 |
| 13 | 191.1 | .124 | .124 | .124 | .124 | .124 |
| 14 | 205.8 | .124 | .125 | .125 | .125 | .125 |
| 15 | 220.5 | .125 | .126 | .125 | .126 | .126 |
| 16 | 235.2 | .126 | .127 | .126 | .127 | .127 |
| Burst Pressure (psi) | | 265 | 280 | 305 | 278 | 260 |
| Direction of Burst | | Axial | Axial | Axial | Axial | Axial |

TABLE 28

BALLOON COMPLIANCE MEASUREMENTS BEFORE TESTING

| | Double Wall Thickness Measurements | | |
|---|---|---|---|
| | Proximal Side-Body | Center | Distal Side-Body |
| 207 | .00175 | .00120 | .00135 |
| 208 | .00145 | .00140 | .00120 |
| 209 | .00130 | .00140 | .00140 |
| 210 | .00140 | .00150 | .00140 |
| 211 | .00165 | .00175 | .00185 |
| 212 | .00135 | .00120 | .00115 |
| 213 | .00150 | .00140 | .00120 |
| 214 | .00135 | .00120 | .00115 |
| 215 | .00155 | .00130 | .00120 |

TABLE 28-continued

BALLOON COMPLIANCE MEASUREMENTS BEFORE TESTING

| | Double Wall Thickness Measurements | | |
|---|---|---|---|
| | Proximal Side-Body | Center | Distal Side-Body |
| 216 | .00135 | .00120 | .00125 |
| 217 | .00140 | .00135 | .00145 |
| 218 | .00165 | .00130 | .00125 |
| 219 | .00145 | .00135 | .00130 |
| 220 | .00155 | .00120 | .00140 |
| 221 | .00135 | .00120 | .00120 |
| 222 | .00155 | .00135 | .00140 |
| 223 | .00140 | .00130 | .00135 |
| 224 | .00145 | .00135 | .00120 |
| 225 | .00160 | .00135 | .00125 |
| 226 | .00150 | .00135 | .00130 |
| 227 | .00155 | .00135 | .00135 |
| 228 | .00155 | .00150 | .00135 |
| 229 | .00150 | .00135 | .00130 |
| 230 | .00135 | .00135 | .00120 |
| 231 | .00160 | .00135 | .00130 |
| 232 | .00160 | .00135 | .00130 |
| 233 | .00140 | .00120 | .00120 |
| 234 | .00145 | .00135 | .00125 |
| 235 | .00150 | .00145 | .00120 |
| 236 | .00145 | .00135 | .00125 |

Examples 237–266

30 balloons were made according to the procedure described above for Examples 1–180.

The balloons were tested according to the procedure described above for Examples 1–180, except that balloons were tested at 1 atm increments from 4–16 atm and then burst.

Tables 29–35 below list certain parameters (PEBAX grade, dimensions, cone angle, rated burst, and hold time representing the total amount of time that the mold was held in the water). The tables also show results of the testing of the expander members.

TABLE 29

BALLOON COMPLIANCE
PEBAX Grade: 6333  
Dimensions (dia. × lgt.): 3.0 × 20 mm  
Cone Angle: 10 degrees  
Rated Burst: 176 psi  
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .114 | .115 | .114 | .114 | .114 |
| 5 | 73.5 | .116 | .118 | .117 | .117 | .117 |
| 6 | 88.2 | .118 | .120 | .120 | .119 | .119 |
| 7 | 102.5 | .120 | .122 | .121 | .121 | .122 |
| 8 | 117.6 | .122 | .123 | .123 | .1230 | .123 |
| 9 | 132.3 | .123 | .124 | .124 | .124 | .125 |
| 10 | 147.0 | .125 | .126 | .1260 | .125 | .126 |
| 11 | 161.7 | .126 | .127 | .127 | .127 | .128 |
| 12 | 176.4 | .128 | .129 | .128 | .128 | .129 |
| 13 | 191.1 | .129 | .130 | .130 | .130 | .131 |
| 14 | 205.8 | .130 | .132 | .132 | .131 | .132 |
| 15 | 220.5 | .132 | .134 | .133 | .133 | .134 |
| 16 | 235.2 | .133 | .135 | .135 | Burst | .135 |
| Burst Pressure (psi) | | 268 | 250 | 250 | 235 | 250 |
| Direction of Burst | | Axial | Axial | Axial | Axial | Axial |

TABLE 30

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .116 | .115 | .115 | .114 | .115 |
| 5 | 73.5 | .119 | .118 | .117 | .117 | .117 |
| 6 | 88.2 | .121 | .120 | .119 | .119 | .119 |
| 7 | 102.5 | .122 | .122 | .121 | .121 | .121 |
| 8 | 117.6 | .124 | .124 | .122 | .1220 | .122 |
| 9 | 132.3 | .125 | .125 | .124 | .124 | .123 |
| 10 | 147.0 | .127 | .126 | .125 | .125 | .125 |
| 11 | 161.7 | .128 | .128 | .126 | .126 | .126 |
| 12 | 176.4 | .129 | .129 | .128 | .127 | .128 |
| 13 | 191.1 | .131 | .131 | .129 | .129 | .129 |
| 14 | 205.8 | .133 | .132 | .131 | .131 | .130 |
| 15 | 220.5 | .135 | .134 | .132 | .132 | .132 |
| 16 | 235.2 | .136 | .135 | .134 | .134 | .133 |
| Burst Pressure (psi) | | 250 | 250 | 250 | 250 | 260 |
| Direction of Burst | | Axial | Axial | Axial | Axial | Axial |

TABLE 31

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .115 | .114 | .116 | .115 | .115 |
| 5 | 73.5 | .118 | .118 | .118 | .118 | .118 |
| 6 | 88.2 | .120 | .120 | .120 | .120 | .120 |
| 7 | 102.5 | .122 | .122 | .122 | .121 | .121 |
| 8 | 117.6 | .123 | .123 | .123 | .123 | .123 |
| 9 | 132.3 | .125 | .125 | .125 | .124 | .124 |
| 10 | 147.0 | .127 | .127 | .126 | .125 | .125 |
| 11 | 161.7 | .128 | .128 | .128 | .127 | .127 |
| 12 | 176.4 | .129 | .130 | .129 | .128 | .128 |
| 13 | 191.1 | .131 | .131 | .131 | .130 | .130 |
| 14 | 205.8 | .133 | .133 | .132 | .131 | .131 |
| 15 | 220.5 | .134 | .135 | .134 | .133 | .132 |
| 16 | 235.2 | .135 | .136 | .136 | .134 | .134 |
| Burst Pressure (psi) | | 250 | 250 | 250 | 250 | 250 |
| Direction of Burst | | Axial | Axial | Axial | Axial | Axial |

TABLE 32

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .114 | .114 | .115 | .114 | .115 |
| 5 | 73.5 | .116 | .117 | .118 | .117 | .118 |
| 6 | 88.2 | .119 | .120 | .120 | .119 | .120 |
| 7 | 102.5 | .121 | .122 | .121 | .121 | .122 |
| 8 | 117.6 | .122 | .123 | .122 | .122 | .123 |
| 9 | 132.3 | .124 | .124 | .124 | .123 | .124 |
| 10 | 147.0 | .125 | .126 | .125 | .125 | .126 |
| 11 | 161.7 | .126 | .127 | .127 | .126 | .126 |
| 12 | 176.4 | .128 | .129 | .129 | .128 | .127 |
| 13 | 191.1 | .130 | .130 | .130 | .129 | .128 |
| 14 | 205.8 | .131 | .131 | .131 | .131 | .131 |
| 15 | 220.5 | .133 | .133 | .133 | .133 | .133 |
| 16 | 235.2 | .135 | .135 | .135 | .135 | .135 |
| Burst Pressure (psi) | | 250 | 250 | 250 | 250 | 250 |
| Direction of Burst | | Axial | Axial | Axial | Axial | Axial |

TABLE 33

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .115 | .115 | .114 | .114 | .115 |
| 5 | 73.5 | .118 | .117 | .117 | .117 | .118 |
| 6 | 88.2 | .120 | .119 | .119 | .118 | .120 |
| 7 | 102.5 | .121 | .120 | .120 | .120 | .122 |
| 8 | 117.6 | .123 | .121 | .121 | .122 | .123 |
| 9 | 132.3 | .124 | .122 | .123 | .123 | .124 |
| 10 | 147.0 | .125 | .123 | .124 | .125 | .125 |
| 11 | 161.7 | .127 | .125 | .125 | .126 | .126 |
| 12 | 176.4 | .128 | .127 | .127 | .128 | .128 |
| 13 | 191.1 | .129 | .129 | .129 | .129 | .130 |
| 14 | 205.8 | .131 | .131 | .130 | .131 | .132 |
| 15 | 220.5 | .132 | .132 | .132 | .133 | .133 |
| 16 | 235.2 | .134 | .134 | .134 | .135 | .134 |
| Burst Pressure (psi) | | 250 | 235 | 250 | 250 | 260 |
| Direction of Burst | | Axial | Axial | Axial | Axial | Axial |

TABLE 34

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .115 | .114 | .114 | .115 | .115 |
| 5 | 73.5 | .118 | .117 | .117 | .117 | .118 |
| 6 | 88.2 | .119 | .119 | .118 | .119 | .120 |
| 7 | 102.5 | .121 | .120 | .120 | .121 | .121 |

TABLE 34-continued

BALLOON COMPLIANCE
PEBAX Grade: 6333
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 8 | 117.6 | .122 | .121 | .121 | .122 | .122 |
| 9 | 132.3 | .123 | .124 | .122 | .123 | .124 |
| 10 | 147.0 | .124 | .125 | .123 | .124 | .125 |
| 11 | 161.7 | .126 | .127 | .125 | .125 | .126 |
| 12 | 176.4 | .128 | .128 | .127 | .127 | .128 |
| 13 | 191.1 | .129 | .130 | .129 | .129 | .129 |
| 14 | 205.8 | .131 | .131 | .130 | .130 | .131 |
| 15 | 220.5 | .133 | .133 | .132 | .132 | .133 |
| 16 | 235.2 | .134 | .135 | .134 | .135 | .135 |
| Burst Pressure (psi) | | 250 | 250 | 268 | 250 | 250 |
| Direction of Burst | | Axial | Axial | Axial | Axial | Axial |

TABLE 35

BALLOON COMPLIANCE MEASUREMENTS BEFORE TESTING
Double Wall Thickness Measurements

| | Proximal Side-Body | Center | Distal Side-Body |
|---|---|---|---|
| 237 | .00155 | .00130 | .00120 |
| 238 | .00135 | .00120 | .00120 |
| 239 | .00125 | .00120 | .00110 |
| 240 | .00125 | .00120 | .00120 |
| 241 | .00130 | .00120 | .00120 |
| 242 | .00135 | .00120 | .00110 |
| 243 | .00130 | .00115 | .00120 |
| 244 | .00130 | .00120 | .00110 |
| 245 | .00135 | .00125 | .00110 |
| 246 | .00135 | .00120 | .00120 |
| 247 | .00135 | .00120 | .00115 |
| 248 | .00125 | .00120 | .00115 |
| 249 | .00120 | .00120 | .00110 |
| 250 | .00130 | .00125 | .00110 |
| 251 | .00130 | .00120 | .00115 |
| 252 | .00135 | .00120 | .00105 |
| 253 | .00130 | .00120 | .00110 |
| 254 | .00120 | .00110 | .00110 |
| 255 | .00120 | .00115 | .00105 |
| 256 | .00125 | .00120 | .00110 |
| 257 | .00125 | .00120 | .00110 |
| 258 | .00135 | .00120 | .00110 |
| 259 | .00135 | .00120 | .00115 |
| 260 | .00120 | .00110 | .00110 |
| 261 | .00130 | .00125 | .00120 |
| 262 | .00130 | .00120 | .00110 |
| 263 | .00125 | .00120 | .00115 |
| 264 | .00130 | .00115 | .00115 |
| 265 | .00135 | .00120 | .00110 |
| 266 | .00120 | .00110 | .00105 |

Examples 267–276

10 balloons were made according to the procedure described above for Examples 1–180, except that parisons had inside diameters of about 0.025 inches and wall thicknesses of about 0.0065 inches.

The balloons were tested according to the procedure described above for Examples 1–180, except that outside diameters were measured at 1 atm increments from 4–16 atms, and then the balloons were burst.

Tables 36–38 below list certain parameters (PEBAX grade, dimensions, cone angle, rated burst, and hold time representing the total amount of time that the mold was held in the water). The tables also show results of the testing of the expander members.

TABLE 36

BALLOON COMPLIANCE
PEBAX Grade: 7033
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .112 | .113 | .113 | .113 | .113 |
| 5 | 73.5 | .116 | .116 | .116 | .116 | .116 |
| 6 | 88.2 | .118 | .118 | .118 | .118 | .118 |
| 7 | 102.5 | .120 | .119 | .120 | .119 | .119 |
| 8 | 117.6 | .121 | .120 | .121 | .120 | .120 |
| 9 | 132.3 | .122 | .121 | .122 | .121 | .121 |
| 10 | 147.0 | .123 | .122 | .124 | .122 | .123 |
| 11 | 161.7 | .124 | .123 | .125 | .124 | .124 |
| 12 | 176.4 | .125 | .125 | .126 | .124 | .125 |
| 13 | 191.1 | .126 | .127 | .127 | .125 | .126 |
| 14 | 205.8 | .127 | .1275 | .128 | .127 | .127 |
| 15 | 220.5 | .128 | .128 | .129 | .1275 | .128 |
| 16 | 235.2 | .129 | .129 | .130 | .1285 | .129 |
| Burst Pressure (psi) | | 263 | 264 | 250 | 264 | 250 |
| Direction of Burst | | Axial | Axial | Axial | Axial | Axial |

TABLE 37

BALLOON COMPLIANCE
PEBAX Grade: 7033
Dimensions (dia. × lgt.): 3.0 × 20 mm
Cone Angle: 10 degrees
Rated Burst: 176 psi
Hold (Secs.) 15

| Pressure | | DIAMETER (inches) Balloon Number | | | | |
|---|---|---|---|---|---|---|
| atm | psi | 237 | 238 | 239 | 240 | 241 |
| 4 | 58.8 | .112 | .114 | .114 | .114 | .113 |
| 5 | 73.5 | .115 | .117 | .116 | .117 | .116 |
| 6 | 88.2 | .117 | .118 | .117 | .118 | .118 |
| 7 | 102.5 | .1185 | .120 | .119 | .120 | .120 |
| 8 | 117.6 | .121 | .121 | .120 | .121 | .122 |
| 9 | 132.3 | .122 | .122 | .121 | .122 | .122 |
| 10 | 147.0 | .123 | .123 | .123 | .123 | .123 |
| 11 | 161.7 | .124 | .124 | .124 | .124 | .124 |
| 12 | 176.4 | .126 | .126 | .125 | .125 | .125 |
| 13 | 191.1 | .128 | .1265 | .127 | .126 | .126 |
| 14 | 205.8 | .128 | .1280 | .128 | .127 | .127 |
| 15 | 220.5 | .129 | .129 | .1295 | .128 | .128 |
| 16 | 235.2 | .130 | .130 | .131 | .129 | .129 |
| Burst Pressure (psi) | | 250 | 264 | 264 | 250 | 264 |
| Direction of Burst | | Axial | Axial | Axial | Axial | Axial |

TABLE 38

BALLOON COMPLIANCE MEASUREMENTS BEFORE TESTING
Double Wall Thickness Measurements

| | Proximal Side-Body | Center | Distal Side-Body |
|---|---|---|---|
| 267 | .00110 | .00110 | .00105 |
| 268 | .00105 | .00105 | .00105 |
| 269 | .00105 | .00100 | .00100 |
| 270 | .00110 | .00110 | .00110 |

TABLE 38-continued

BALLOON COMPLIANCE MEASUREMENTS BEFORE TESTING
Double Wall Thickness Measurements

|     | Proximal Side-Body | Center | Distal Side-Body |
|-----|--------------------|--------|------------------|
| 271 | .00115             | .00110 | .00100           |
| 272 | .00115             | .00100 | .00100           |
| 273 | .00115             | .00110 | .00100           |
| 274 | .00115             | .00100 | .00105           |
| 275 | .00110             | .00110 | .00100           |
| 276 | .00110             | .00100 | .00100           |

Examples 277–306

30 balloons were made according to the procedure described above for Examples 1–180, except that cone angles were 26° and the parison inside diameter was 0.025 inches with a wall thickness of 0.0065, The balloons were tested according to the procedure described above for Examples 1–180, except that outside diameters were measured at 1 atm increments from 4–16 atms, and then the balloons were burst.

Tables 39–41 below list certain parameters (PEBAX grade, dimensions, cone angle, rated burst, and hold time representing the total amount of time that the mold was held in the water). The tables also show results of the testing of the expander members.

TABLE 39

BALLOON COMPLIANCE
PEBAX Grade: 7033
Dimensions (dia. × lgt.): 3.0 × 20 mm
Cone Angle: 26°
Rated Burst: 176
Hold (Secs.) 15

| Pressure | DIAMETER (cm) Balloon Numbers | | | | | | | | | |
|---|---|---|---|---|---|---|---|---|---|---|
| atm | 277 | 278 | 279 | 280 | 281 | 282 | 283 | 284 | 285 | 286 |
| 4 | 2.9972 | 3.0226 | 2.9718 | 2.9210 | 2.9210 | 2.9210 | 2.8448 | 2.8194 | 2.8956 | 2.9210 |
| 5 | 3.0988 | 3.1242 | 3.0988 | 3.0226 | 2.9972 | 2.9972 | 2.9972 | 2.99.72. | 3.0226 | 3.0480 |
| 6 | 3.1496 | 3.1750 | 3.1496 | 3.1242 | 30.7340 | 3.1496 | 30.9880 | 3.0988 | 3.1750 | 3.1496 |
| 7 | 3.2004 | 3.2258 | 3.2004 | 3.1750 | 3.1750 | 3.2258 | 3.2004 | 3.2004 | 3.2258 | 3.2004 |
| 8 | 3.2766 | 3.2512 | 3.2258 | 3.2258 | 3.2258 | 3.2766 | 3.2512 | 3.2512 | 3.2766 | 3.3020 |
| 9 | 3.3020 | 3.3020 | 3.2766 | 3.2766 | 3.2766 | 3.3528 | 3.3020 | 3.3020 | 3.3274 | 3:3528 |
| 10 | 3.3528 | 3.3528 | 3.3274 | 3.3030 | 3.3274 | 3.4036 | 3.3528 | 3.3528 | 3.4036 | 3.4036 |
| 11 | 3.3782 | 3.4036 | 3.3782 | 3.3528 | 3.3782 | 3.4544 | 3.4036 | 3.4036 | 3.4544 | 3.4544 |
| 12 | 3.4544 | 3.4544 | 3.4290 | 3.4036 | 3.4036 | 3.5052 | 3.4544 | 3.4544 | 3.5306 | 3.5306 |
| 13 | 3.5052 | 3.4798 | 3.5052 | 3.4290 | 3.4544 | 3.5814 | 3.5052 | 3.5052 | 3.5814 | 3.6068 |
| 14 | 3.5560 | 3.5560 | 3.5814 | 3.5052 | 3.5052 | 3.6576 | 3.5560 | 3.5560 | 3.6576 | 3.6576 |
| 15 | 3.5814 | 3.6068 | 3.6068 | 3.5306 | 3.5306 | 3.7338 | 3.6068 | 3.6322 | 3.8100 | 3.7592 |
| 16 | 3.6576 | 3.6830 | 3.6322 | 3.6068 | 3.6068 | 3.8608 | 3.6576 | 3.6576 | 3.8100 | 3.8100 |
| Burst psi | 290 | 265 | 265 | 295 | 260 | 265 | 265 | 260 | 250 | 265 |
| atm | 19.70 | 18.02 | 18.02 | 20.06 | 17.68 | 18.02 | 18.02 | 17.68 | 17.00 | 18.02 |

TABLE 40

BALLOON COMPLIANCE
PEBAX Grade: 7033
Dimensions (dia. × lgt.): 3.0 × 20 mm
Cone Angle: 26°
Rated Burst: 176
Hold (Secs.) 15

| Pressure | DIAMETER (cm) Balloon Numbers | | | | | | | | | |
|---|---|---|---|---|---|---|---|---|---|---|
| atm | 287 | 288 | 289 | 290 | 291 | 292 | 293 | 294 | 295 | 296 |
| 4 | 2.8956 | 2.8956 | 2.9210 | 2.8702 | 2.8956 | 2.9718 | 2.8956 | 2.9464 | 2.9210 | 2.8702 |
| 5 | 2.9972 | 2.9972 | 3.0480 | 2.9972 | 3.0226 | 3.0988 | 3.0226 | 3.0734 | 3.0480 | 2.9718 |
| 6 | 3.1242 | 3.0988 | 3.1496 | 3.0988 | 3.1242 | 3.1750 | 3.1242 | 3.1750 | 3.1242 | 3.0734 |
| 7 | 3.2004 | 3.2004 | 3.2258 | 3.1496 | 3.1750 | 3.2512 | 3.1750 | 3.2258 | 3.2004 | 3.1750 |
| 8 | 3.2512 | 3.2258 | 3.3020 | 3.2258 | 3.2512 | 3.3020 | 3.2258 | 3.2766 | 3.2512 | 3.2258 |

TABLE 40-continued

BALLOON COMPLIANCE
PEBAX Grade: 7033
Dimensions (dia. × lgt.): 3.0 × 20 mm
Cone Angle: 26°
Rated Burst: 176
Hold (Secs.) 15

| Pressure | DIAMETER (cm) Balloon Numbers | | | | | | | | | |
|---|---|---|---|---|---|---|---|---|---|---|
| atm | 287 | 288 | 289 | 290 | 291 | 292 | 293 | 294 | 295 | 296 |
| 9 | 3.3274 | 3.3020 | 3.3528 | 3.2766 | 3.3020 | 3.3528 | 3.2766 | 3.3274 | 3.3274 | 3.2766 |
| 10 | 3.3782 | 3.3528 | 3.4036 | 3.3274 | 3.3528 | 3.4036 | 3.3274 | 3.3782 | 3.3782 | 3.3274 |
| 11 | 3.4290 | 3.4036 | 3.4798 | 3.3782 | 3.4036 | 3.4544 | 3.3782 | 3.4290 | 3.4290 | 3.3782 |
| 12 | 3.4798 | 3.4544 | 3.5560 | 3.4290 | 3.4544 | 3.5052 | 3.4290 | 3.5052 | 3.4798 | 3.4290 |
| 13 | 3.5560 | 3.5306 | 3.6068 | 3.4798 | 3.5052 | 3.5306 | 3.4544 | 3.5560 | 3.5560 | 3.4798 |
| 14 | 3.6068 | 3.5560 | 3.6576 | 3.5306 | 3.5560 | 3.5306 | 3.5052 | 3.6068 | 3.6068 | 3.5052 |
| 15 | 3.6576 | 36068 | 3.7338 | 3.5814 | 3.6322 | 3.5306 | 3.5306 | 3.6830 | 3.6830 | 3.5814 |
| 16 | 3.7592 | 3.6576 | 3.8354 | 3.6576 | 3.7084 | 3.5560 | 3.5560 | 3.7592 | 3.6830 | 3.6322 |
| Burst psi | 265 | 265 | 265 | 265 | 265 | 265 | 265 | 260 | 250 | 265 |
| atm | 18.02 | 18.02 | 18.02 | 18.02 | 18.02 | 18.02 | 18.02 | 17.68 | 17.00 | 18.02 |

TABLE 41

BALLOON COMPLIANCE
PEBAX Grade: 7033
Dimensions (dia. × lgt.): 3.0 × 20 mm
Cone Angle: 26°
Rated Burst: 176
Hold (Secs.) 15

| Pressure | DIAMETER (cm) Balloon Numbers | | | | | | | | | |
|---|---|---|---|---|---|---|---|---|---|---|
| atm | 297 | 298 | 299 | 300 | 301 | 302 | 303 | 304 | 305 | 306 |
| 4 | 2.8702 | 2.8956 | 2.8194 | 2.8194 | 2.8702 | 2.7940 | 2.8448 | 2.8702 | 2.8956 | 2.8448 |
| 5 | 2.9972 | 2.9972 | 2.9972 | 2.9210 | 2.9972 | 2.9972 | 2.9972 | 2.9718 | 2.9972 | 2.9972 |
| 6 | 3.1242 | 3.1242 | 3.0988 | 3.0480 | 3.0988 | 3.1242 | 3.0988 | 3.0734 | 3.0988 | 3.0988 |
| 7 | 3.1750 | 3.1750 | 3.2004 | 3.1496 | 3.1750 | 3.2004 | 3.1750 | 3.1496 | 3.1750 | 3.2004 |
| 8 | 3.2512 | 3.2512 | 3.2512 | 3.2004 | 3.2258 | 3.2512 | 3.2512 | 3.2004 | 3.2258 | 3.2766 |
| 9 | 3.3274 | 3.3020 | 3.2766 | 3.2512 | 3.3020 | 3.3274 | 3.3020 | 3.2512 | 3.2766 | 3.3274 |
| 10 | 3.3782 | 3.3528 | 3.3274 | 3.3274 | 3.3528 | 3.4036 | 3.3274 | 3.3020 | 3.3274 | 3.4036 |
| 11 | 3.4544 | 3.4036 | 3.3782 | 3.3782 | 3.4036 | 3.4544 | 3.3782 | 3.3782 | 3.3782 | 3.4544 |
| 12 | 3.5052 | 3.4798 | 3.4555 | 3.4036 | 3.4544 | 3.5052 | 3.4544 | 3.4290 | 3.4290 | 3.5052 |
| 13 | 3.5560 | 3.5052 | 3.5306 | 3.4544 | 3.5052 | 3.6068 | 3.5052 | 3.4544 | 3.4798 | 3.5814 |
| 14 | 3.6322 | 3.5306 | 3.5814 | 3.5052 | 3.5560 | 3.6576 | 3.5560 | 3.5052 | 3.5306 | 3.6322 |
| 15 | 3.6830 | 3.5814 | 3.6322 | 3.5560 | 3.6322 | 3.7592 | 3.6068 | 3.5560 | 3.5814 | 3.7084 |
| 16 | 3.7846 | 3.6322 | 3.7084 | 3.6322 | 3.6830 | 3.8100 | 3.6830 | 3.6322 | 3.6322 | 3.7846 |
| Burst psi | 265 | 260 | 265 | 265 | 265 | 265 | 265 | 265 | 265 | 265 |
| atm | 18.02 | 17.68 | 18.02 | 18.02 | 18.02 | 18.02 | 18.02 | 18.02 | 18.02 | 18.02 |

Examples 307–366

60 balloons were made according to the following procedure: Tubing was placed into a mold and preheated for 15–30 seconds to a preselected balloon blowing temperature. The tubing was stretched and inflated to make a balloon. The balloon was allowed to remain at the balloon blowing temperature for 15–30 seconds, and then elevated to at least the crystallization temperature for 10–20 seconds. The balloon was then cooled to room temperature and removed from the mold.

The balloons were tested according to the procedure described above for Examples 1–180.

Tables 42–47 below list certain parameters (PEBAX grade, dimensions, crystallization temperature, mold temperature, left and right stretch dimensions, nitrogen pressure, and air flow). The tables also show results of the testing of the expander members.

TABLE 42

PEBAX GRADE: 6333
BALLOON DIMENSIONS (diameter × length): 3 × 20 mm

PARAMETERS:

| TEMP: | CRYSTALIZATION: | 200° F. | MOLD: | 190° F. |
|---|---|---|---|---|
| STRETCH: | LEFT: | 2.60 INCHES | RIGHT: | 2.60 INCHES |
| PSI: | 350 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 307 | 0.00120 | 0.00120 | 0.00130 | .020 × .035 | 0.119 | 0.128 | 0.135 | 238 |
| 308 | 0.00120 | 0.00130 | 0.00120 | .020 × .035 | 0.118 | 0.127 | 0.137 | 241 |
| 309 | 0.00135 | 0.00135 | 0.00145 | .020 × .035 | 0.118 | 0.128 | 0.136 | 245 |
| 310 | 0.00130 | 0.00140 | 0.00120 | .020 × .035 | 0.117 | 0.127 | 0.137 | 238 |
| 311 | 0.00125 | 0.00135 | 0.00145 | .020 × .035 | 0.117 | 0.127 | 0.134 | 240 |
| 312 | 0.00135 | 0.00125 | 0.00125 | .020 × .035 | | | | 249 |
| 313 | 0.00125 | 0.00125 | 0.00125 | .020 × .035 | | | | 239 |
| 314 | 0.00135 | 0.00130 | 0.00130 | .020 × .035 | | | | 230 |
| 315 | 0.00130 | 0.00130 | 0.00130 | .020 × .035 | | | | 240 |
| 316 | 0.00130 | 0.00130 | 0.00135 | .020 × .035 | | | | 240 |
| Average | 0.001285 | 0.0013 | 0.001305 | .020 × .035 | 0.1178 | 0.1274 | 0.1358 | 240 |
| Standard | 5.79751E − 05 | 5.7735E − 05 | 8.95979E − 05 | | 0.000837 | 0.000548 | 0.001304 | 4.898979 |

Calculated k-stat (psi): 214.5106
Calculated Hoop Stress (psi): 23794.55

TABLE 43

PEBAX GRADE: 6333
BALLOON DIMENSIONS (diameter × length): 3 × 20 mm

PARAMETERS:

| TEMP: | CRYSTALIZATION: | 200° F. | MOLD: | 190° F. |
|---|---|---|---|---|
| STRETCH: | LEFT: | 2.75 INCHES | RIGHT: | 2.75 INCHES |
| PSI: | 350 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 317 | 0.00130 | 0.00135 | 0.00130 | .020 × .035 | 0.116 | 0.127 | 0.135 | 240 |
| 318 | 0.00135 | 0.00140 | 0.00140 | .020 × .035 | 0.114 | 0.127 | 0.135 | 248 |
| 319 | 0.00135 | 0.00145 | 0.00135 | .020 × .035 | 0.116 | 0.127 | 0.134 | 240 |
| 320 | 0.00135 | 0.00145 | 0.00145 | .020 × .035 | 0.115 | 0.127 | 0.134 | 251 |
| 321 | 0.00130 | 0.00145 | 0.00130 | .020 × .035 | 0.115 | 0.127 | 0.135 | 240 |
| 322 | 0.00145 | 0.00135 | 0.00135 | .020 × .035 | | | | 240 |
| 323 | 0.00140 | 0.00140 | 0.06140 | .020 × .035 | | | | 248 |
| 324 | 0.00135 | 0.00135 | 0.00140 | .020 × .035 | | | | 240 |
| 325 | 0.00135 | 0.00135 | 0.00135 | .020 × .035 | | | | 240 |
| 326 | 0.00135 | 0.00135 | 0.00135 | .020 × .035 | | | | 240 |
| Average | 0.001355 | 0.00138 | 0.00137 | .020 × .035 | 0.1152 | 0.127 | 0.1346 | 242.7 |
| Standard | 4.38E − 05 | 4.216E − 05 | 4.74342E − 05 | | 0.000837 | 1.86E − 09 | 0.000548 | 4.423423 |

Calculated K-stat (psi): 219.6549
Calculated Hoop Stress (psi): 22747.53

TABLE 44

PEBAX GRADE: 7033
BALLOON DIMENSIONS (diameter × length): 3 × 30 mm

PARAMETERS:

| TEMP: | CRYSTALIZATION: | 200° F. | MOLD: | 190° F. |
|---|---|---|---|---|
| STRETCH: | LEFT: | 2.75 INCHES | RIGHT: | 2.75 INCHES |
| PSI: | 380 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 327 | 0.00130 | 0.001350 | 0.00130 | .020 × .035 | 0.115 | 0.125 | 0.129 | 270 |
| 328 | 0.00125 | 0.001300 | 0.00130 | .020 × .035 | 0.116 | 0.125 | 0.129 | 270 |
| 329 | 0.00130 | 0.001350 | 0.00130 | .020 × .035 | 0.116 | 0.125 | 0.132 | 270 |
| 330 | 0.00130 | 0.001300 | 0.00125 | .020 × .035 | 0.115 | 0.127 | 0.132 | 263 |
| 331 | 0.00125 | 0.001300 | 0.00130 | .020 × .035 | 0.116 | 0.126 | 0.132 | 270 |
| 332 | 0.00135 | 0.001350 | 0.00130 | .020 × .035 | | | | 280 |
| 333 | 0.00135 | 0.001300 | 0.00130 | .020 × .035 | | | | 280 |
| 334 | 0.00130 | 0.001300 | 0.00130 | .020 × .035 | | | | 270 |
| 335 | 0.00125 | 0.001250 | 0.00120 | .020 × .035 | | | | 283 |
| 336 | 0.00130 | 0.001200 | 0.00130 | .020 × .035 | | | | 240 |
| Average | 0.001295 | 0.0013 | 1.285E − 03 | .020 × .035 | 0.1156 | 0.1256 | 0.1308 | 269.6 |
| Standard | 3.69E − 05 | 4.714E − 05 | 3.37474E − 05 | | 0.000548 | 0.000894 | 0.001643 | 12.09408 |

Calculated K-stat (psi): 206.6745
Calculated Hoop Stress (psi): 26148.08

TABLE 45

PEBAX GRADE: 7033
BALLOON DIMENSIONS (diameter × length): 3 × 30 mm

PARAMETERS:

| TEMP: | CRYSTALIZATION: | 260° F. | MOLD: | 210° F. |
|---|---|---|---|---|
| STRETCH: | LEFT: | 2.25 INCHES | RIGHT: | 2.25 INCHES |
| PSI: | 320 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 337 | 0.00100 | 0.00100 | 0.00100 | .020 × .035 | 0.121 | 0.13 | 0.138 | 238 |
| 338 | 0.00115 | 0.00120 | 0.00100 | .020 × .035 | 0.121 | 0.129 | 0.136 | 230 |
| 339 | 0.00100 | 0.00105 | 0.00115 | .020 × .035 | 0.121 | 0.13 | 0.138 | 220 |
| 340 | 0.00110 | 0.00115 | 0.00100 | .020 × .035 | 0.121 | 0.129 | 0.136 | 219 |
| 341 | 0.00105 | 0.00110 | 0.00100 | .020 × .035 | 0.121 | 0.129 | 0.137 | 238 |
| 342 | 0.00105 | 0.00100 | 0.00100 | .020 × .035 | | | | 239 |
| 343 | 0.00120 | 0.00120 | 0.00105 | .020 × .035 | | | | 238 |
| 344 | 0.00100 | 0.00110 | 0.00105 | .020 × .035 | | | | 238 |
| 345 | 0.00100 | 0.00105 | 0.00105 | .020 × .035 | | | | 220 |
| 346 | 0.00105 | 0.00110 | 0.00100 | .020 × .035 | | | | 239 |
| Average | 0.00106 | 0.001095 | 0.00103 | .020 × .035 | 0.121 | 0.1294 | 0.137 | 231.9 |
| Standard | 6.99E − 05 | 7.245E − 05 | 4.83046E − 05 | | 0 | 0.000548 | 0.001 | 8.83742 |

Calculated k-stat (psi): 185.9189
Calculated Hoop Stress (psi): 28309.3

TABLE 46

PEBAX GRADE: 7233
BALLOON DIMENSIONS (diameter × length): 3 × 20 mm

PARAMETERS:

| | | | | |
|---|---|---|---|---|
| TEMP: | CRYSTALIZATION: | 400° F. | MOLD: | 190° F. |
| STRETCH: | LEFT: | 2 INCHES | RIGHT: | 2 INCHES |
| PSI: | 400 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 347 | 0.00140 | 0.00140 | 0.00140 | .020 × .035 | 0.113 | 0.119 | 0.124 | 305 |
| 348 | 0.00145 | 0.00150 | 0.00145 | .020 × .035 | 0.111 | 0.119 | 0.124 | 330 |
| 349 | 0.00145 | 0.00150 | 0.00150 | .020 × .035 | 0.113 | 0.122 | 0.124 | 315 |
| 350 | 0.00140 | 0.00140 | 0.00140 | .020 × .035 | 0.115 | 0.122 | 0.125 | 313 |
| 351 | 0.00150 | 0.00145 | 0.00140 | .020 × .035 | 0.113 | 0.120 | 0.124 | 343 |
| 352 | 0.00145 | 0.00145 | 0.00135 | .020 × .035 | | | | 343 |
| 353 | 0.00150 | 0.00150 | 0.00140 | .020 × .035 | | | | 329 |
| 354 | 0.00140 | 0.00150 | 0.00140 | .020 × .035 | | | | 303 |
| 355 | 0.00140 | 0.00140 | 0.00140 | .020 × .035 | | | | 313 |
| 356 | 0.00140 | 0.00150 | 0.00140 | .020 × .035 | | | | 330 |
| Average | 0.001433 | 0.00146 | 0.00141 | .020 × .035 | 0.113 | 0.1204 | 0.1242 | 322.4 |
| Standard | 4.33E − 05 | 4.595E − 05 | 3.94405E − 05 | | 0.001414 | 0.001517 | 0.000447 | 14.59985 |

Calculated K-stat (psi): 246.437
Calculated Hoop Stress (psi): 27081.6

TABLE 47

PEBAX GRADE: 7233
BALLOON DIMENSIONS (diameter × length): 3 × 20 mm

PARAMETERS:

| | | | | |
|---|---|---|---|---|
| TEMP: | CRYSTALIZATION: | 260° F. | MOLD: | 210° F. |
| STRETCH: | LEFT: | 2.25 INCHES | RIGHT: | 2.25 INCHES |
| PSI: | 330 | | | |
| AIRFLOW: | 200 | | | |

| Balloon No. | Double Centerwall Thickness (inches) | Double Proximal Wall Thickness (inches) | Double Distal Wall Thickness (inches) | Measured ID/OD (inches) | Diameter 50 psi (inches) | Diameter 100 psi (inches) | Diameter 150 psi (inches) | Burst Pressure (psi) |
|---|---|---|---|---|---|---|---|---|
| 357 | 0.00110 | 0.00100 | 0.00125 | .020 × .035 | 0.118 | 0.125 | 0.128 | 240 |
| 358 | 0.00100 | 0.00105 | 0.00115 | .020 × .035 | 0.119 | 0.125 | 0.13 | 260 |
| 359 | 0.00100 | 0.00105 | 0.00120 | .020 × .035 | 0.118 | 0.123 | 0.128 | 242 |
| 360 | 0.00110 | 0.00120 | 0.00100 | .020 × .035 | 0.119 | 0.126 | 0.131 | 245 |
| 361 | 0.00110 | 0.00120 | 0.00120 | .020 × .035 | 0.119 | 0.125 | 0.13 | 260 |
| 362 | 0.00100 | 0.00100 | 0.00120 | .020 × .035 | | | | 260 |
| 363 | 0.00120 | 0.00120 | 0.00130 | .020 × .035 | | | | 242 |
| 364 | 0.00115 | 0.00105 | 0.00120 | .020 × .035 | | | | 262 |
| 365 | 0.00100 | 0.00105 | 0.00120 | .020 × .035 | | | | 260 |
| 366 | 0.00110 | 0.00100 | 0.00115 | .020 × .035 | | | | 231 |
| Average | 0.001075 | 0.00108 | 0.001185 | .020 × .035 | 0.1156 | 0.1248 | 0.1294 | 250.2 |
| Standard | 7.17E − 05 | 8.5635E − 05 | 7.83511E − 05 | | 0.000548 | 0.001095 | 0.001342 | 11.34117 |

Calculated K-stat (psi): 191.192
Calculated Hoop Stress (psi): 29046.47

FIGS. 4–15 were prepared by collecting data according to material type, and reducing the data to a series of quadratic equations that include stretch, crystallization temperature, and balloon blowing temperature as dependant variables. The equations were then plotted using a statistical design of experiments program called ECHIP®. Response variables of interest were then plotted.

With regard to FIGS. 4–15, the balloons were expanded to two times their original length in the axial direction.

The foregoing specification and figures are presented for the purpose of illustrating, and not limiting, the present invention.

What is claimed is:

1. A balloon for an angioplasty device having single polymeric layer comprising a blend of at least one polymer material selected from each of Groups A and B, wherein Group A consists of polyesteretheramide copolymers, Group B consists of polyamide polymers, polyester copolymers, polyurethane copolymers, polyethylene, and combinations thereof, and at least 20 weight percent of the blend is Group A polymer material and at least 2 weight percent of the blend is Group B polymer material.

2. The balloon of claim 1 wherein the Group A polymer material is a polyesteretheramide block copolymer.

3. The balloon of claim 2 wherein the polyesteretheramide block copolymer has a hardness of from about 45 Shore D to about 78 Shore D.

4. The balloon of claim 3 wherein the polyesteretheramide block copolymer has a hardness of from about 55 Shore D to about 75 Shore D.

5. The balloon of claim 4 wherein the polyesteretheramide block copolymer has a hardness of from about 63 to about 72 Shore D.

6. The balloon of claim 1 wherein at least 40 weight percent of the blend is Group A polymer material.

7. The balloon of claim 1 wherein at least 80 weight percent of the blend is Group A polymer material.

8. The balloon of claim 1 wherein at least 91 weight percent of the blend is Group A polymer material.

9. The balloon of claim 1 wherein the Group B polymer material comprises a polyamide polymer in an amount of at least 2 weight percent of the blend.

10. The balloon of claim 9 wherein the polyamide is selected from the group consisting of nylon 11, nylon 12, nylon 6, nylon 6/6, nylon 4/6.

11. The balloon of claim 1 wherein the Group B polymer material comprises a polymer selected from the group consisting of polyester copolymers, polyurethane copolymers, polyethylene, and combinations thereof, in an amount of at least 2% by weight of the blend.

* * * * *

UNITED STATES PATENT AND TRADEMARK OFFICE
CERTIFICATE OF CORRECTION

PATENT NO. : 6,200,290 B1  
DATED : March 13, 2001  
INVENTOR(S) : Burgmeier

Page 1 of 2

It is certified that error appears in the above-identified patent and that said Letters Patent is hereby corrected as shown below:

<u>Column 7,</u>
Table 3, Balloon #22, Diameter 100 psi Column; delete "0.121," insert -- 0.120 --.
Table 4, 4th line; delete "Hot Pot 212°," insert -- Hot Pot 210° --
Table 4, Balloon #31, Double Centerwall column; delete "0.00170," insert -- 0.00140 --
Table 4, Balloon #31, Burst Pressure Column; delete "293," insert -- 153 --
Table 4, Balloon #35, Double Centerwall column; delete "0.00130," insert -- 0.00140 --
Table 4, Balloon #36, Double Centerwall column; delete "0.00130," insert -- 0.00140 --

<u>Column 9,</u>
Table 5, 4th line; delete "Hot Pot 212°," insert -- Hot Pot 210° --
Table 5, line 26; delete "Calculated Hoop Stress (psi) 22097," insert -- Calculated Hoop Stress (psi) 21097 --
Table 6, 4th line; delete "Hot Pot 212°," insert -- Hot Pot 200° --

<u>Column 11,</u>
Table 7, 4th line; delete "Hot Pot 212°," insert -- Hot Pot 210° --
Table 8, Balloon #76, Double Centerwall column ; delete "0.00150," insert --0.00160 --

<u>Column 13,</u>
Table 9, Balloon #83, Double Proximal column; delete "0.00139," insert -- 0.00130 --

<u>Column 26,</u>
Table 25, atm #8, psi Column; delete "11.6," insert -- 117.6 --

<u>Column 27,</u>
Table 28, #212, Distal Side Body Column; delete ".00115," insert -- . 00125 --

<u>Column 29,</u>
Table 30, line 9; delete "237, 238, 239, 240, 241," insert -- 242, 243, 244, 245, 246 --
Table 31, line 9; delete "237, 238, 239, 240, 241," insert -- 247, 248, 249, 250, 251 --
Table 32, line 9; delete "237, 238, 239, 240, 241," insert -- 252, 253, 254, 255, 256 --

<u>Column 30,</u>
Table 32 continued, line 9; delete "237, 238, 239, 240, 241," insert --252, 253, 254, 255, 256 --
Table 33, line 9; delete "237, 238, 239, 240, 241," insert -- 257, 258, 259, 260, 261 --
Table 34, line 9; delete "237, 238, 239, 240, 241," insert -- 262, 263, 264, 265, 266 --

UNITED STATES PATENT AND TRADEMARK OFFICE
CERTIFICATE OF CORRECTION

PATENT NO. : 6,200,290 B1
DATED : March 13, 2001
INVENTOR(S) : Burgmeier

It is certified that error appears in the above-identified patent and that said Letters Patent is hereby corrected as shown below:

Column 31,
Table 34 continued, line 9; delete "237, 238, 239, 240, 241," insert -- 262, 263, 264, 265, 266 --

Column 32,
Table 36, line 9; delete "237, 238, 239, 240, 241," insert -- 267, 268, 269, 270, 271 --
Table 37, line 9; delete "237, 238, 239, 240, 241," insert -- 272, 273, 274, 275, 276 --

Column 34,
Table 39, atm #5, 284 column; delete "2.99.72," insert -- 2.9972 --

Column 35,
Table 40 continued, atm #15, 288 column; delete "36068," insert -- 3.6068 --

Column 37,
Table 43, line 26; delete "Calculated K-stat (psi) 219.6549" insert -- Calculated K-stat (psi) 219.6849 --

Signed and Sealed this

Twenty-fifth Day of September, 2001

Attest:

NICHOLAS P. GODICI
Attesting Officer    Acting Director of the United States Patent and Trademark Office